(12) United States Patent
Guillerez et al.

(10) Patent No.: US 7,335,471 B2
(45) Date of Patent: Feb. 26, 2008

(54) POLYPEPTIDES DERIVED FROM RNA POLYMERASES AND USE THEREOF

(75) Inventors: Jean Guillerez, Gif sur Yvette (FR); Pascal Lopez, Paris (FR); Marc Dreyfus, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 454 days.

(21) Appl. No.: 10/472,146

(22) PCT Filed: Mar. 19, 2002

(86) PCT No.: PCT/FR02/00961

§ 371 (c)(1),
(2), (4) Date: Dec. 23, 2003

(87) PCT Pub. No.: WO02/074964

PCT Pub. Date: Sep. 26, 2002

(65) Prior Publication Data

US 2004/0091854 A1 May 13, 2004

(30) Foreign Application Priority Data

Mar. 19, 2001 (FR) ................................. 01 03677

(51) Int. Cl.
*C12Q 1/68* (2006.01)
*C12P 19/34* (2006.01)
(52) U.S. Cl. ......................................... 435/6; 435/91.3
(58) Field of Classification Search ...................... None
See application file for complete search history.

(56) References Cited

U.S. PATENT DOCUMENTS 5,385,834 A 1/1995 Ikeda
6,107,037 A 8/2000 Sousa et al.

OTHER PUBLICATIONS

Olga V Makarova et al.: "Transcribing of *Excherichia coli* genes with mutant T7 RNA polymerases: Stability of lacZ mRNA inversely correlates with polymerase speed." Proceedings of the National Academy of Sciences of the United States, vol. 92, No. 26, 1995, pp. 12250-12254, XP002189160 1995 ISSN: 0027-8424.

Gary Bonner et al: "Characterization of a set of T7 RNA polymerase active site mutants." Journal of Biological Chemistry, vol. 269, No. 40, 1994, pp. 225120-25128, XP002189161 ISSN: 0021-9258.

M Frugier et al: "Synthetic Polymines Stimulate in Vitro Transcription by T7 RNA Polymerase" Nucleic Acids Research, Oxford University Press, Surrey GB, vol. 22, No. 14, 1994, pp. 2784-2790, XP002926452 ISSN: 0305-1048.

Jin Ding Jun "A mutant RNA polymerase reveals a kinetic mechanism for the switch between non productive stuttering synthesis and productive initiation during promoter clearance." Journal of Biological Chemistry, vol. 271, No. 20, 1996, pp. 11659-11667, XP002189159 ISSN: 0021-9258.

Pascal J Lopez et al: "The low processitivity of T7 RNA polymerase over the initially transcribed sequence can limit productive initiation in vivo." Journal of Molecular Biology, vol. 269, No. 1, 1997, pp. 41-51, XP002189162 ISSN: 0022-2836.

*Primary Examiner*—Gary Benzion
*Assistant Examiner*—David C. Thomas
(74) *Attorney, Agent, or Firm*—Young & Thompson

(57) ABSTRACT

Mutant RNA polymerases of phagic origin in which the peptide chain is modified by substitution, deletion or addition of at least one amino acid, the modification having the effect of reducing the sensitivity of the RNA polymerases to the initial transcription sequence of the DNA sequence coding for the RNA, for a method for production of the RNA, or proteins coded by the RNA, from given nucleotide sequences, comprising a sequence of DNA coding for the RNA, the transcription of which is placed under the control of a promoter recognised by wild-type RNA polymerases and the mutant RNA polymerases as above. The method has a higher yield of RNA than the yield obtained when using the wild-type RNA polymerases in the presence of the same non-consensual ITS as that found in the sequence of DNA coding for the RNA.

3 Claims, 4 Drawing Sheets

POLYPEPTIDES DERIVED FROM RNA POLYMERASES AND USE THEREOF

Figure 1:
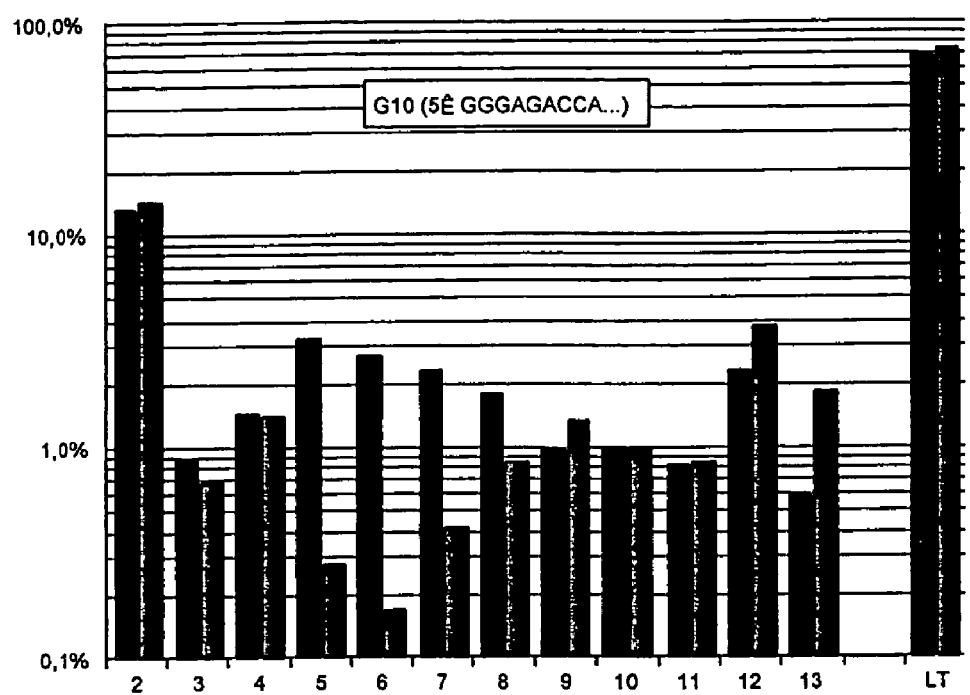
Figure 2:
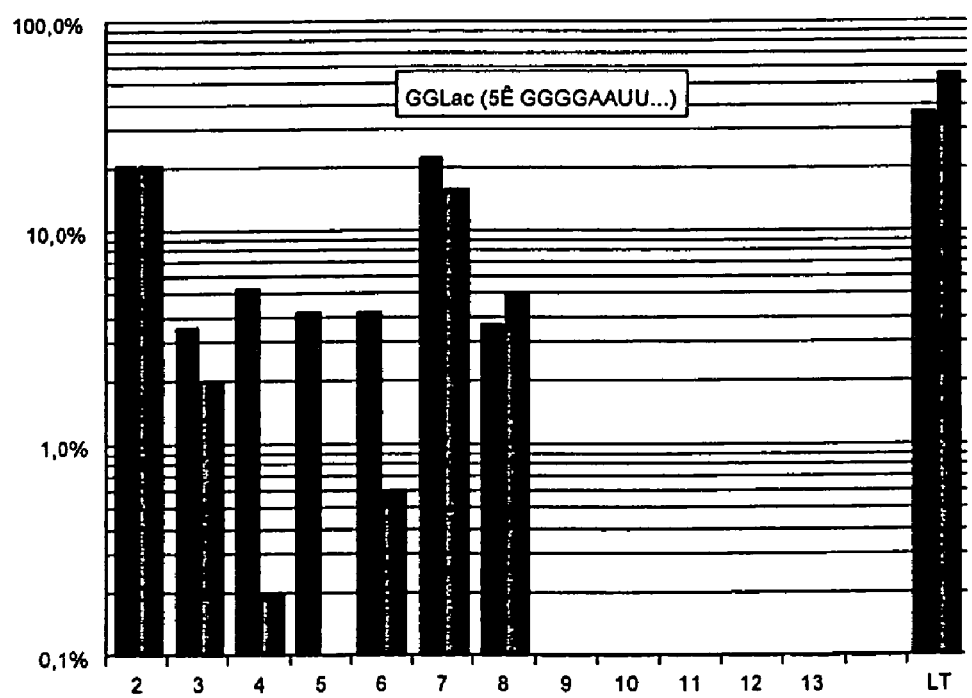
Figure 3:
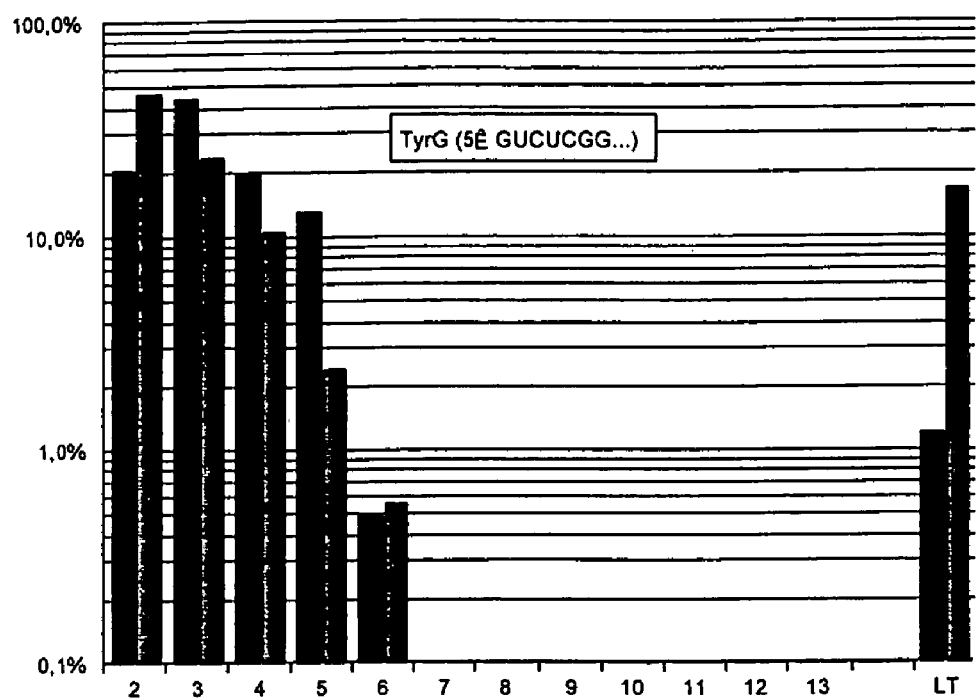
Figure 4:
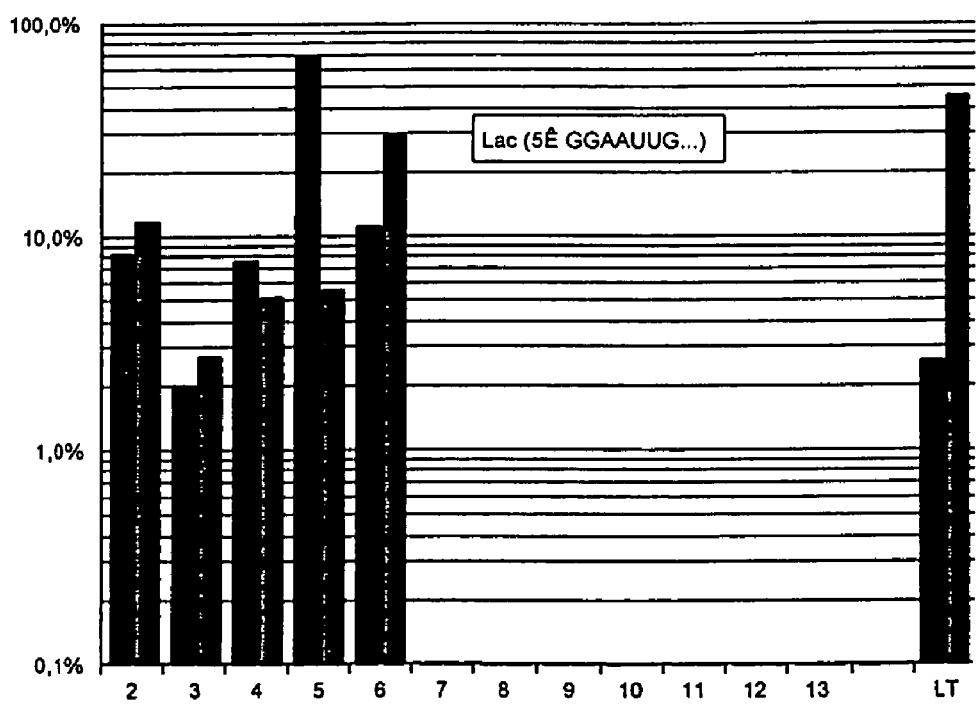
Figure 5:
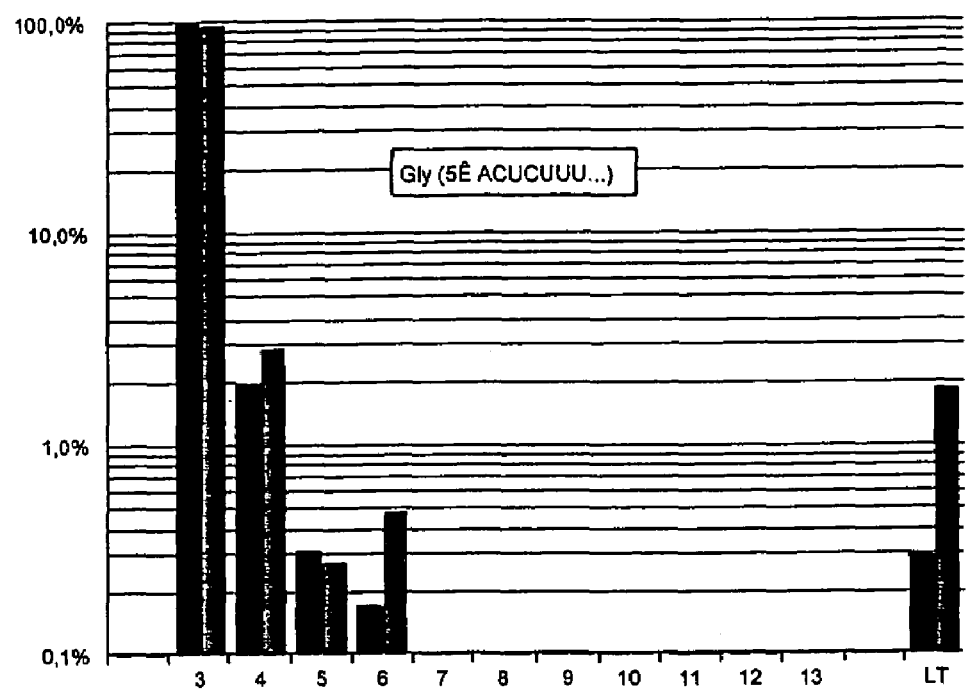
Figure 6:
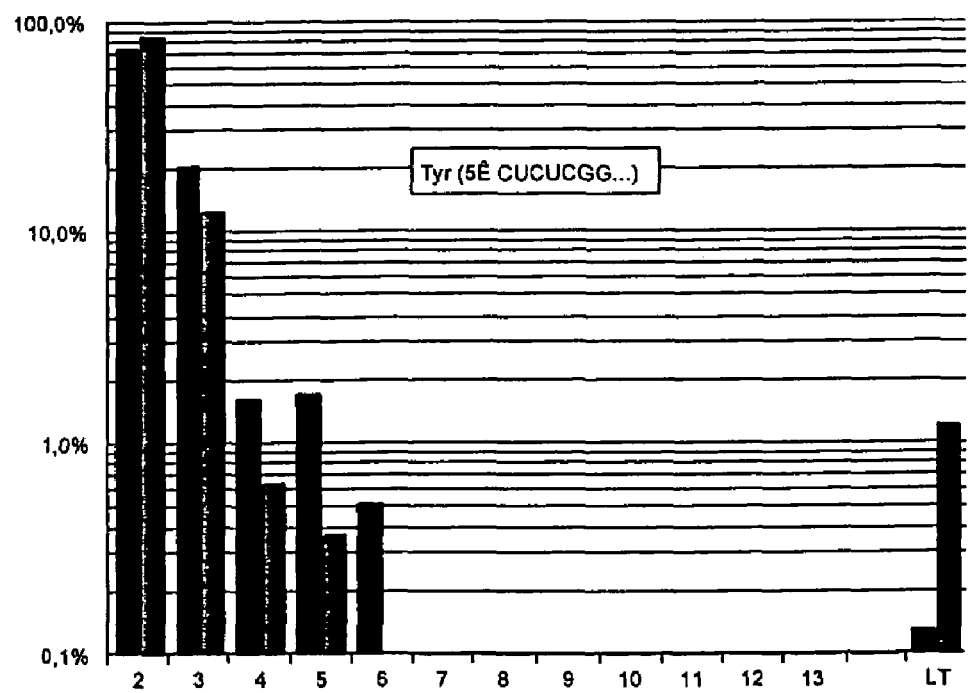

A subject of the present invention is polypeptides derived from RNA polymerases, also designated mutated RNA polymerases, as well as their uses, in particular in the field of in vivo or in vitro preparation of RNA of interest.

When obtaining large quantities of DNA molecules of perfectly defined sequence, high purity and small size (10 to 100 nt) chemical synthesis is at present the most economical method. There are now in the market a very large number of enterprises which carry out these syntheses on request. These same companies also offer the chemical synthesis of RNA but the technology is such that the cost, which is at least ten times higher than for DNA, is at present prohibitive.

Enzyme synthesis is therefore favoured, using an RNA polymerase coupled to a DNA matrix, chemically synthesized or of plasmid origin, which comprises the sequence to be transcribed downstream of the promoter sequence of the polymerase used. The necessary elements (polymerases, rNTP, cloning vectors) are available on the market in the form of optimized kits.

Bacteriophage T7 RNA polymerase is very widely used for carrying out transcription reactions in vitro with the aim of synthesizing large quantities (up to a milligram) of RNA from matrices of recombinant DNA. These RNAs synthesized in vitro are necessary for a number of uses in Biology, the Biotechnologies and Pharmacy; the following can be mentioned inter alia:
  translation in vitro.
  the study of RNA maturation.
  the effect of anti-sense RNA on gene expression.
  RNA-protein interactions.
  the synthesis of homologues of small cell RNAs (tRNA, rRNA).
  the production of ribozymes.

More generally these RNAs are also used as molecular probes and structural study substrates.

A few T7 polymerase mutants have already been described. These are mutated RNA polymerases derived from the wild-type T7 RNA polymerase, and comprising one of the following mutations:
  replacement of the lysine (K) in position 222 by glutamic acid; this RNA polymerase thus mutated has the property of recognizing a promoter altered by mutation, and is described in U.S. Pat. No. 5,385,834,
  replacement of the tyrosine (Y) in position 639 by a phenylalanine (F); this RNA polymerase thus mutated has the property of incorporating deoxyribonucleotides instead of ribonucleotides, thus allowing the synthesis of DNA instead of RNA, and is described in U.S. Pat. No. 6,107,037,
  replacement of the isoleucine (I) in position 810 by a serine (S); this RNA polymerase thus mutated has the property of being slower than the wild-type RNA polymerase, and is described in Bonner et al., The Journal of Biochemical Chemistry, 269, pp. 25120-25128 (1994).

The problem to be resolved by the present invention, is linked with the fact that the activity on a given DNA matrix of the T7 RNA polymerase (and moreover of all the other known RNA polymerases) is strongly dependent on the nature of the first 6-12 nucleotides transcribed (Initial Transcribed Sequence, or ITS) of the nucleotide sequence coding for a given RNA (Milligan et al., 1987). If the ITS differs too much from the consensus sequence 5'GGGAGA . . . then the polymerase frequently aborts and a large quantity of the ribonucleoside triphosphates is consumed in order to synthesize small abortive RNAs to the detriment of the desired large RNAs.

Therefore, the experimenter is generally compelled, in order to obtain an effective transcription, to modify the sequence that is to be transcribed, in order to add to it a favourable ITS (also referred to as consensus or consensual ITS). In a number of cases, this constraint is very annoying, even unacceptable.

A potential method for obtaining any non-consensual 5' end RNA uses an after treatment of an RNA comprising the desired sequence downstream of a consensus ITS; the latter (target) RNA can therefore be produced in abundance. Moreover it is necessary to chemically synthesize a chimeric DNA-RNA oligonucleotide the DNA sequence of which is complementary to the 3' end of the RNA to be eliminated, then the hybrid that can form the oligo with the target transcript is digested by RNase H. This complex and onerous method is justified if the desired RNA is of a very large size and if its 5' end must be rigorously defined. (Li et al. 1999, Lapham et al. 1997).

The addition, to the reaction medium, of synthetic polyamines can increase the production of RNA by, it appears, reducing the number of abortive cycles; however determination of the optimum experimental conditions (choice of polyamine, concentration of use) requires case-by-case research. Moreover it should be noted that the effect of these polyamines is weak, even non-existent, when the matrix is of plasmid origin (double strand) (Frugier et al. 1994).

These two methods use reagents which are not in common use (specific polyamines or oligonucleotides) and are unsuitable for routine use. It is evident that the possibility of having, at the start, a polymerase which by nature aborts less would be a much simpler way of resolving the difficulty.

The invention results from the demonstration by the Inventors of the fact that modifying the peptide sequence of the RNA polymerases could reduce the sensitivity of the RNA polymerases thus modified to the nature of the ITS of the nucleotide sequences to be transcribed.

The invention aims to provide polypeptides derived from wild-type RNA polymerases usually used in the production of RNA of interest, which are distinctly less sensitive to the nature of the non-consensual ITS than said wild-type RNA polymerases.

The invention also aims to provide new processes for producing RNA of interest with yields greater than those of the processes using wild-type RNA polymerases when the latter are sensitive to the ITS of the nucleotide sequence coding for said RNA of interest.

A subject of the invention is the use of mutated RNA polymerases of phage origin, namely of RNA polymerases originating from phages, the peptide chain of which is modified, with respect to the wild-type RNA polymerases from which they derive, by substitution, or deletion, or addition of at least one amino acid, this modification having the effect of reducing the sensitivity of said RNA polymerases to the ITS contained in the DNA sequence coding for an RNA of interest, for the implementation of a process for producing said RNA of interest, or of proteins coded by this RNA of interest, starting with determined nucleotide sequences comprising a DNA sequence coding for said RNA of interest and the transcription of which is placed under the control of a promoter recognized by the abovementioned wild-type RNA polymerases and mutated RNA polymerases, said process having a production yield of said RNA greater than the yield obtained in the case of use of the wild-type RNA polymerases (in the presence of the same non-consensual ITS as that contained in the DNA sequence coding for said RNA of interest).

The activity of said RNA polymerases thus mutated within the transcription of the DNA sequence coding for said RNA of interest is distinctly less affected by the nature of the nucleotides constituting the non-consensual ITS of this DNA sequence, which is not that of the wild-type RNA polymerases from which they derive, which allows these mutated RNA polymerases to be up to approximately 40 times more active than the wild-type polymerases, and therefore, in the abovementioned process of the present invention, to be characterized by a production yield of said RNA greater than the yield obtained in the case of use of the wild-type RNA polymerases in the presence of this same non-consensual ITS.

According to another particularly advantageous aspect of the invention, the mutated RNA polymerases of the invention make it possible to obtain RNA of interest with a practically identical yield, whatever the ITS present in the sequence coding for said RNA of interest.

Advantageously, the use of the abovementioned mutated RNA polymerases allows the implementation of a process for producing RNA of interest, the yield of which is up to approximately ten times greater than the yield obtained in the case of use of the wild-type RNA polymerases in the presence of a non-consensual ITS.

The RNA of interest capable of being produced in greater quantity within the implementation of a process according to the invention using the abovementioned mutated RNA polymerases, are natural or chimeric RNAs, said RNAs if appropriate comprising one or more non-canonical nucleoside monophosphates (namely for example a deoxyribose instead of a ribose, said sugar itself being able optionally to carry an analogue of one of the natural nucleic bases if this analogue is recognized as such by the polymerase). In the latter case, a subject of the present invention is also the use of the above-mentioned process using said above-mentioned RNA polymerases, in the implementation of a method for determining the sequence of a nucleic acid molecule.

The mutated RNA polymerases used are advantageously those deriving from wild-type phage monomeric polymerases, in particular those originating from monomeric RNA polymerases of bacteriophages such as T7, T3, K11, SP6, respectively described in particular in the article by W. T. McAllister and C. A. Raskin, Molecular Microbiology (1993), 10(1), 1-6.

Preferably the abovementioned mutated RNA polymerases are those deriving from the wild-type RNA polymerases at least one of the amino acids of which, situated between positions 1 and approximately 410, in particular approximately between positions 90 and 320, more particularly between positions 115 and 300, is modified by substitution or deletion.

Advantageously, the mutated RNA polymerases used are those comprising a leucine in position 266, substituted for the proline situated in position 266 in the wild-type T7 RNA polymerase, or the proline situated in homologous position in the wild-type RNA polymerases of bacteriophages, such as the proline situated in positions 267 in T3, 289 in K11, and 239 in SP6.

A more particular subject of the invention is the abovementioned use of any mutated RNA polymerase as defined above, the proline of which, defined above, and/or at least one of the amino acids situated in the vicinity of the abovementioned proline, namely an amino acid situated at a distance less than or equal to approximately 10 angströms from the proline in question, when said RNA polymerase is considered in its three-dimensional structure (as described in Cheetham, G. M. & Steitz, T. A. (1999), Science 286, 2305-2309; Cheetham, G. M. et al., Nature 399, 80-83; Sousa, R. et al., Nature 364, 593-599), is modified by substitution or deletion.

The invention also relates to the abovementioned use of the particularly preferred mutated RNA polymerases chosen from the following:

those derived from the wild-type T7 RNA polymerase, and comprising at least one of the following mutations:
  replacement of the isoleucine (I) in position 117 by a valine (V),
  replacement of the isoleucine (I) in position 119 by a valine (V),
  replacement of the valine (V) in position 134 by an alanine (A),
  replacement of the aspartic acid (D) in position 147 by asparagine (N),
  replacement of the histidine (H) in position 230 by an arginine (R),
  replacement of the proline (P) in position 266 by a leucine (L),
  replacement of the arginine (R) in position 291 by a cysteine (C), those derived from the wild-type T3 RNA polymerase, and comprising at least one of the following mutations:
  replacement of the aspartic acid (D) in position 148 by asparagine (N),
  replacement of the proline (P) in position 267 by a leucine (L),
  replacement of the arginine (R) in position 292 by a cysteine (C), those derived from the wild-type K11 RNA polymerase, and comprising at least one of the following mutations:
  replacement of the aspartic acid (D) in position 167 by asparagine (N),
  replacement of the proline (P) in position 289 by a leucine (L),
  replacement of the arginine (R) in position 314 by a cysteine (C), those derived from the wild-type SP6 RNA polymerase, and comprising at least one of the following mutations:
  replacement of the aspartic acid (D) in position 117 by asparagine (N),
  replacement of the proline (P) in position 239 by a leucine (L).

A more particular subject of the invention is the abovementioned use of the following mutated RNA polymerases:
  the mutated T7 RNA polymerase represented by SEQ ID NO: 2, comprising a leucine in position 266 substituted for the proline,
  the mutated T7 RNA polymerase represented by SEQ ID NO: 4, comprising a valine in position 117 substituted for the isoleucine, and an alanine in position 134 substituted for the valine,
  the mutated T7 RNA polymerase represented by SEQ ID NO: 6, comprising a valine in position 119 substituted for the isoleucine, and an asparagine in position 147 substituted for the aspartic acid,
  the mutated T7 RNA polymerase represented by SEQ ID NO: 8, comprising an arginine in position 230 substituted for the histidine, and a cysteine in position 291 substituted for the arginine,
  the mutated T7 RNA polymerase represented by SEQ ID NO: 10, comprising a leucine in position 266 substituted for the proline, and a phenylalanine in position 639 substituted for the tyrosine, the mutated T7 RNA polymerase represented by SEQ ID NO: 12, comprising an asparagine in position 810 substituted for the isoleucine, the mutated T7 RNA polymerase represented by SEQ ID NO: 14, comprising a leucine in position 266 substituted for the proline, and an asparagine in position 810 substituted for the isoleucine, the mutated T7 RNA polymerase represented by SEQ ID NO: 16, comprising a valine in position 119 substituted for the isoleucine, an asparagine in position 147 substituted for the aspartic acid, and an asparagine in position 810 substituted for the isoleucine.

A subject of the invention is also the use described above of abovementioned mutated RNA polymerases comprising as well as the modification(s) of amino acid(s) defined above, the modification, by substitution, or deletion, or addition, of at least one other amino acid involved in a mechanism other than that of sensitivity to the ITS within the scope of the transcription of DNA sequences, such as a modification of an amino acid making it possible for the RNA polymerase thus modified to incorporate non-canonical nucleoside triphosphates (for example dNTP) in an RNA chain, and therefore making it possible to synthesize DNA, and/or a modification of an amino acid making it possible to obtain a slower RNA polymerase, and therefore, in association with a mutation of the invention, making it possible to improve the synthesis yields of proteins of interest.

A more particular subject of the invention is therefore the abovementioned use of mutated RNA polymerases as defined above, comprising as well as the mutation(s) defined above, a mutation corresponding to the substitution of the tyrosine in position 639 in T7, or in analogous position in the other polymerases defined above, by a phenylalanine, and/or a mutation corresponding to the substitution of the isoleucine in position 810 in T7, or in analogous position in the other polymerases defined above, by a serine, or by an asparagine.

Therefore, the invention also relates more particularly to the use of the abovementioned mutated T7 RNA polymerase represented by SEQ ID NO: 10.

A subject of the invention is also:

the mutated RNA polymerases derived from the wild-type T7 RNA polymerase comprising at least one of the abovementioned mutations in position 117, 119, 134, 147, 230, 266, or 291, and optionally at least one of the following additional mutations:

replacement of the tyrosine (Y) in position 639 by a phenylalanine (F), replacement of the isoleucine (I) in position 810 by an asparagine (N), the mutated RNA polymerases derived from the wild-type T3 RNA polymerase comprising at least one of the abovementioned mutations in position 148, 267, or 292, and optionally at least one of the following additional mutations:

replacement of the tyrosine (Y) in position 640 by a phenylalanine (F), replacement of the isoleucine (I) in position 811 by an asparagine (N), the mutated RNA polymerases derived from the wild-type K11 RNA polymerase comprising at least one of the abovementioned mutations in position 167, 289, or 314, and optionally at least one of the following additional mutations:

replacement of the tyrosine (Y) in position 662 by a phenylalanine (F), replacement of the isoleucine (I) in position 833 by an asparagine (N), the mutated RNA polymerases derived from the wild-type SP6 RNA polymerase comprising at least one of the abovementioned mutations in position 117 or 239, and optionally at least one of the following additional mutations:

replacement of the tyrosine (Y) in position 631 by a phenylalanine (F), replacement of the isoleucine (I) in position 804 by an asparagine (N).

The invention also relates to any process for preparing mutated RNA polymerases of phage origin as defined above, namely of RNA polymerases, the determined nucleotide sequence transcription activity of which, comprising a DNA sequence coding for an RNA of interest and the transcription of which is placed under the control of a promoter recognized by the mutated RNA polymerases and by the wild-type RNA polymerases of phage origin from which they originate, is greater than the transcription activity of this determined sequence by the wild-type RNA polymerases, in particular preparation of mutated RNA polymerases being up to approximately 40 times more active than said wild-type RNA polymerases within the scope of the implementation of processes for producing RNA of interest starting with said determined nucleotide sequence, said process comprising:

a stage of modification of the peptide chain of the wild-type RNA polymerases of phage origin by substitution, or deletion or addition of at least one codon of the gene coding for said wild-type RNA polymerases, and transformation of appropriate cells, such as *E. coli*, with vectors containing the gene thus modified, detection of the abovementioned cells producing mutated RNA polymerases for which the production yield of a particular marker within appropriate cells, such as *E. coli*, in particular within the abovementioned cells, such as a marker of resistance to an antibiotic, or a chromogenic marker, coded by a nucleotide sequence inserted downstream of the promoter recognized by the abovementioned RNA polymerases, this promoter and the sequence coding for the marker being separated by an ITS, the nature of approximately the first 6 to 12 nucleotides of which is known to affect the activity of the wild-type RNA polymerases, is greater than the production yield of this same marker obtained by use of the wild-type RNA polymerases under the same conditions, purification of the abovementioned mutated RNA polymerases from the cells detected in the preceding stage.

A more particular subject of the invention is the abovementioned use of mutated RNA polymerases of phage origin as obtained by implementation of the preparation process defined above.

The invention also relates to mutated RNA polymerases of phage origin as obtained by implementation of a preparation process defined above.

A more particular subject of the invention is the mutated RNA polymerases of phage origin as obtained by implementation of a preparation process defined above, originating from the modification of wild-type phage monomeric polymerases, in particular originating from monomeric RNA polymerases of bacteriophages such as T7, T3, K11, SP6.

A subject of the invention is also the abovementioned mutated RNA polymerases of phage origin deriving from the RNA polymerases of wild-type phage origin, at least one of the amino acids of which, situated between positions 1 and approximately 410, in particular approximately between positions 90 and 320, more particularly between positions 115 and 300, is modified by substitution or deletion, to the exclusion of the mutated RNA polymerase derived from the wild-type T7 RNA polymerase, and comprising the following mutation:
replacement of the lysine (K) in position 222 by glutamic acid.

A more particular subject of the invention is the abovementioned mutated RNA polymerases comprising a leucine in position 266, substituted for the proline in position 266 in the wild-type T7 RNA polymerase, or in the homologous positions in the wild-type bacteriophage RNA polymerases, such as positions 267 in T3, 289 in K11, and 239 in SP6.

A more particular subject of the invention is also any mutated RNA polymerase as defined above, of which the proline defined above, and/or at least one of the amino acids situated in the vicinity of the abovementioned proline, namely an amino acid situated at a distance less than or equal to approximately 10 angströms from the proline in question, when said RNA polymerase is considered in its three-dimensional structure, is modified by substitution or deletion.

The invention more particularly relates to the mutated RNA polymerases derived from the wild-type RNA polymerases such as T7, T3, K11 or SP6, and chosen from the following:
those derived from the wild-type T7 RNA polymerase, and comprising at least one of the following mutations:
replacement of the isoleucine (I) in position 117 by a valine (V),
replacement of the isoleucine (I) in position 119 by a valine (V),
replacement of the valine (V) in position 134 by an alanine (A),
replacement of the aspartic acid (D) in position 147 by asparagine (N),
replacement of the histidine (H) in position 230 by an arginine (R),
replacement of the proline (P) in position 266 by a leucine (L),
replacement of the arginine (R) in position 291 by a cysteine (C),
said mutated RNA polymerases optionally comprising at least one of the following additional mutations:
replacement of the tyrosine (Y) in position 639 by a phenylalanine (F),
replacement of the isoleucine (I) in position 811 by an asparagine (N),
those derived from the wild-type T3 RNA polymerase, and comprising at least one of the following mutations:
replacement of the aspartic acid (D) in position 148 by asparagine (N),
replacement of the proline (P) in position 267 by a leucine (L),
replacement of the arginine (R) in position 292 by a cysteine (C),
said mutated RNA polymerases optionally comprising at least one of the following additional mutations:
replacement of the tyrosine (Y) in position 640 by a phenylalanine (F),
replacement of the isoleucine (I) in position 811 by an asparagine (N),
those derived from the wild-type K11 RNA polymerase, and comprising at least one of the following mutations:
replacement of the aspartic acid (D) in position 167 by asparagine (N),
replacement of the proline (P) in position 289 by a leucine (L),
replacement of the arginine (R) in position 314 by a cysteine (C),
said mutated RNA polymerases optionally comprising at least one of the following additional mutations:
replacement of the tyrosine (Y) in position 662 by a phenylalanine (F),
replacement of the isoleucine (I) in position 833 by an asparagine (N),
those derived from the wild-type SP6 RNA polymerase, and comprising at least one of the following mutations:
replacement of the aspartic acid (D) in position 117 by asparagine (N),
replacement of the proline (P) in position 239 by a leucine (L),
said mutated RNA polymerases optionally comprising at least one of the following additional mutations:
replacement of the tyrosine (Y) in position 631 by a phenylalanine (F),
replacement of the isoleucine (I) in position 804 by an asparagine (N).

A more particular subject of the invention is the following mutated RNA polymerases:
the mutated T7 RNA polymerase represented by SEQ ID NO: 2, comprising a leucine in position 266 substituted for the proline,
the mutated T7 RNA polymerase represented by SEQ ID NO: 4, comprising a valine in position 117 substituted for the isoleucine, and an alanine in position 134 substituted for the valine,
the mutated T7 RNA polymerase represented by SEQ ID NO: 6, comprising a valine in position 119 substituted for the isoleucine, and an asparagine in position 147 substituted for the aspartic acid,
the mutated T7 RNA polymerase represented by SEQ ID NO: 8, comprising an arginine in position 230 substituted for the histidine, and a cysteine in position 291 substituted for the arginine,
the mutated T7 RNA polymerase represented by SEQ ID NO: 10, comprising a leucine in position 266 substituted for the proline, and a phenylalanine in position 639 substituted for the tyrosine,
the mutated T7 RNA polymerase represented by SEQ ID NO: 12, comprising an asparagine in position 810 substituted for the isoleucine,
the mutated T7 RNA polymerase represented by SEQ ID NO: 14, comprising a leucine in position 266 substituted for the proline, and an asparagine in position 810 substituted for the isoleucine,
the mutated T7 RNA polymerase represented by SEQ ID NO: 16, comprising a valine in position 119 substituted for the isoleucine, an asparagine in position 147 substituted for the aspartic acid, and an asparagine in position 810 substituted for the isoleucine.

The invention also relates to the nucleotide sequences coding for a mutated RNA polymerase of phage origin as defined above.

Therefore a more particular subject of the invention is the nucleotide sequences SEQ ID NO: 1, 3, 5, 7, 9, 11, 13, 15, coding respectively for the abovementioned proteins SEQ ID NO: 2, 4, 6, 8, 10, 12, 14, 16, or any nucleotide sequence derived from the abovementioned nucleotide sequences by degeneration of the genetic code and retaining the property of coding for the abovementioned proteins.

A subject of the invention is also any vector, in particular any plasmid, containing a nucleotide sequence as defined above.

A subject of the invention is also any cell transformed by an abovementioned vector, said cell being chosen in particular from those of bacteria (E. coli for example), yeasts, or higher eukaryotes.

The invention also relates to any process for preparing the abovementioned mutated RNA polymerases of phage origin, comprising the culture of transformed cells defined above in an appropriate culture medium, and the purification of the RNA polymerases produced by said cells.

A subject of the invention is also any process for preparing in vitro RNA of interest, comprising the bringing together, in an appropriate medium, of at least one mutated RNA polymerase of phage origin as defined above, with the determined nucleotide sequences comprising a DNA sequence coding for said RNA of interest and the transcription of which is placed under the control of a promoter recognized by the abovementioned wild-type RNA polymerases and mutated RNA polymerases.

The invention also relates to any process for preparing in vivo RNA of interest, comprising the culture of cells as defined above, said cells producing at least one mutated RNA polymerase of phage origin according to the invention, and the genome of which has been modified in order to contain determined nucleotide sequences comprising a DNA sequence coding for said RNA of interest and the transcription of which is placed under the control of a promoter recognized by the abovementioned wild-type RNA polymerases and mutated RNA polymerases.

A subject of the invention is also any process for preparing in vivo proteins of interest comprising the culture of cells as defined above, said cells producing at least one mutated RNA polymerase of phage origin according to the invention, and the genome of which has been modified in order to contain determined nucleotide sequences comprising a DNA sequence coding for said proteins of interest and the transcription of which is placed under the control of a promoter recognized by the abovementioned wild-type RNA polymerases and mutated RNA polymerases.

Advantageously, in the case of the implementation of processes for preparing proteins of interest as described above, the mutated RNA polymerases produced by the cells, are chosen from SEQ ID NO: 12, 14 and 16.

The invention also relates to any process for preparing in vitro or in vivo RNA or proteins of interest, as described above, and comprising, moreover, a stage of addition of synthetic polyamines as described by Frugier et al. Amongst the polyamines capable of being used, the following can be mentioned:

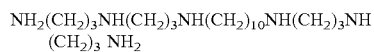

The invention is further illustrated using the following detailed description of the production of mutated RNA polymerases of phage origin according to the invention, and of their use for increasing the production of determined RNAs with respect to the production of these same RNAs using wild-type RNA polymerases.

Whilst the RNA polymerase of the bacteriophage T7 is normally very processive in the elongation phase, this is not the case during the transcription of the ITS: in this case, there is a high probability that the nascent transcript will be prematurely released (abortive transcription) (Martin et al., 1988). This is the number of abortive cycles that the enzyme must achieve, on average, before successfully transcribing the ITS and entering the elongation phase, which determines the frequency with which the complete transcripts are synthesized (Ikeda, 1992). This number is minimal when the ITS corresponds to the 5' sequence of the class III genes of the bacteriophage T7 ('consensual' ITS: 5' GGGAGA . . . ). However, even under these conditions, the abortive transcripts make up a large proportion (40% to 60%) of the total transcripts. This proportion increases very rapidly when the ITS is removed from the consensus, or when the RNA polymerase carries mutations which reduce its rate of elongation, increasing the time necessary for the crossing of the ITS (Bonner et al., 1994; Bonner et al., 1992). Optionally, the combination of a non-consensual ITS and a slow polymerase leads to a situation where the enzyme loops indefinitely in the abortive phase: no large transcript is then synthesized. This property can be observed not only in vitro, but also in vivo, in cells of Escherichia coli expressing T7 RNA polymerase (Lopez et al., 1997; Makarova et al., 1995). It is the latter situation that we have exploited in order to select mutants of T7 RNA polymerase, the activity of which is less sensitive to the nature of the ITS than that of the wild-type enzyme.

We placed a target gene, the expression of which is easily detectable—the lacZ gene, the product of which is β-galactosidase—preceded by a non-consensual ITS, under the control of the T7 promoter. This gene is then introduced into a bacterial cell containing moreover a plasmid coding for a T7 polymerase mutated in its catalytic site (i.e. a 'slow' polymerase). As indicated above, the system, blocked in abortive phase, does not produce large transcripts, and therefore no β-galactosidase. However, after random mutagenesis of the plasmid, it is possible to select bacterial clones which synthesize new mutants of the enzyme which are capable of expressing the target gene. Apart from the reverse mutants of the initial mutation of the catalytic site, we thus isolated mutations in the N-terminal part of the enzyme, which is not involved in the catalysis. When these new mutations were introduced into the wild-type enzyme, i.e. without mutations at the catalytic site, we observed that they reduced the susceptibility of the enzyme to the exact nature of the ITS. This is the point mutant P266L which is more particularly described here and forms the subject of the present invention. In fact, it makes it possible to transcribe, at usable levels, matrices on which the wild-type enzyme is practically inoperative.

DETAILED DESCRIPTION a) Preparation, Purification and Storage

The point mutant SEQ ID NO: 2 obtained corresponds to the change in the sequence of the T7 polymerase of Proline 266 to Leucine (P266L). The gene of this mutated T7 polymerase is included in the pAR1219 plasmid under the control of an inducible promoter (pLac UV5). The protein (polymerase) is over-expressed in the BL 21 (ompF-) strain of E. coli. The protocols for extraction, purification and storage of the purified protein are identical to those of the wild-type polymerase. In order to facilitate the purification, the polymerase was labelled with six N-terminal histidines by transfer of the mutated region in place of the equivalent coding sequence of the pBH 161 plasmid. (He et al. 1977). This label in no way modifies the catalytic properties of the polymerase. It is then sufficient to pass the bacterial supernatant over a Nickel affinity column in order to obtain >90% pure protein. Storage for a long duration (2 years) at −20° C. does not alter the properties of the enzyme.

b) Catalytic Activity.

Under the standard conditions used for the wild-type polymerase, the mutant is also capable of converting all the rNTPs provided to it to RNA. However the rate at which this incorporation is carried out is approximately three times lower for the mutant, i.e. a complete transcription will require a longer period of time (e.g. 6 hours instead of 2 hours).

As referred to below, the main distinction between the wild-type polymerase and the mutant is to be found at the level of distribution as a function of the size (and therefore of the mass) of the RNAs obtained. Two types of RNA can be observed on completion of in vitro transcription: abortive RNAs and large RNAs.

We present below the in vitro transcription results obtained with the wild-type polymerase and the mutant on seven very different ITSs. The matrices are plasmid DNAs (approximately 6 kbp) linearized at restriction sites situated from 31 to 78 nt downstream of the promoter. The reactions are stopped at 10, 20 or 30 minutes depending on the case, and the marking is $\alpha^{32}$PGTP, $\alpha^{32}$PUTP or $\gamma^{32}$PGTP. The experimental conditions used are described in J. Mol. Biol. (1997) 269:41-51. The transcripts are separated on a high resolution denaturing polyacrylamide gel.

G10 (5' GGGAGACCA . . . linearized at 33 nt) carries the consensual ITS. In fact in this case the first 30 nucleotides correspond to gene 10 sequence of the phage T7, one of those better transcribed by T7 polymerase.

GGLac (5' GGGGAAUU. linearized at 69 nt) carries the ITS that is found in the commercial plasmid pET15b (Novagen) which comprises the binding site of the Lac repressor in order to optionally repress the T7 transcription.

Lac (5' GGAAUUG. linearized at 30 nt) is a plasmid equivalent to the preceding one, in which the operative site is close to 2 nucleotides of the promoter.

TyrG (5' GUCUCGG. linearized at 78 nt), Gly (5' ACUCUUU. linearized at 71 nt), Tyr (5' CUCUCGG. linearized at 78 nt) and Val (5' GGUUUCG. linearized at 31 nt) are plasmids corresponding to matrices intended to synthesize in vitro tRNAs or fragments of tRNA and deemed difficult to transcribe (Frugier et al., 1994)

Figure 7:
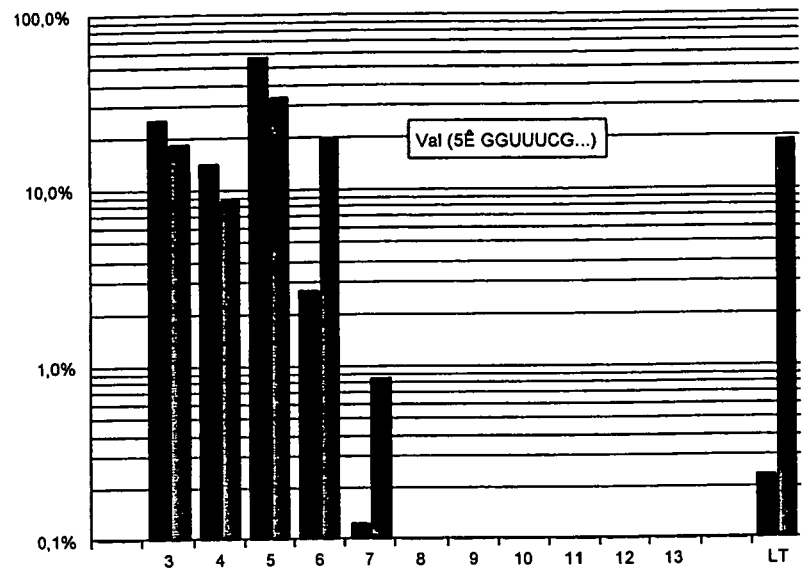

FIGS. 1 to 7 show the detailed results indicating the abortive RNAs observed, their percentage with respect to the total number of transcripts, as well as the equivalent figures for the long transcripts which escaped the abortive phase, in the case of use of wild-type T7 polymerase (also designated wt, and represented using black columns) and of the use of the mutated RNA polymerase SEQ ID NO: 2 (also designated P266L, and represented using grey columns) in the presence of the ITS G10 (FIG. 1), GGLac (FIG. 2), TyrG (FIG. 3), Lac (FIG. 4), Gly (FIG. 5), Tyr (FIG. 6), Val (FIG. 7). The abortive transcripts are distributed between the 2 mer and the 13 mer (numbering 2 to 13 along the x-axis). The transcripts originating from polymerases which have escaped the abortive phase are identified as long transcripts (LT along the x-axis). A logarithmic scale is used along the y-axis in order to make it possible to quantify transcripts which are not very abundant.

These results show clearly that in all cases the mutant has less difficulty than the wild-type polymerase in incorporating the fifth, sixth and seventh nucleotides. If at these positions the polymerase has and/or must incorporate a pyrimidine (U or C) the abortion rate is raised for the wild-type polymerase and the removal of the handicap by the mutant is all the greater.

Figure 8:
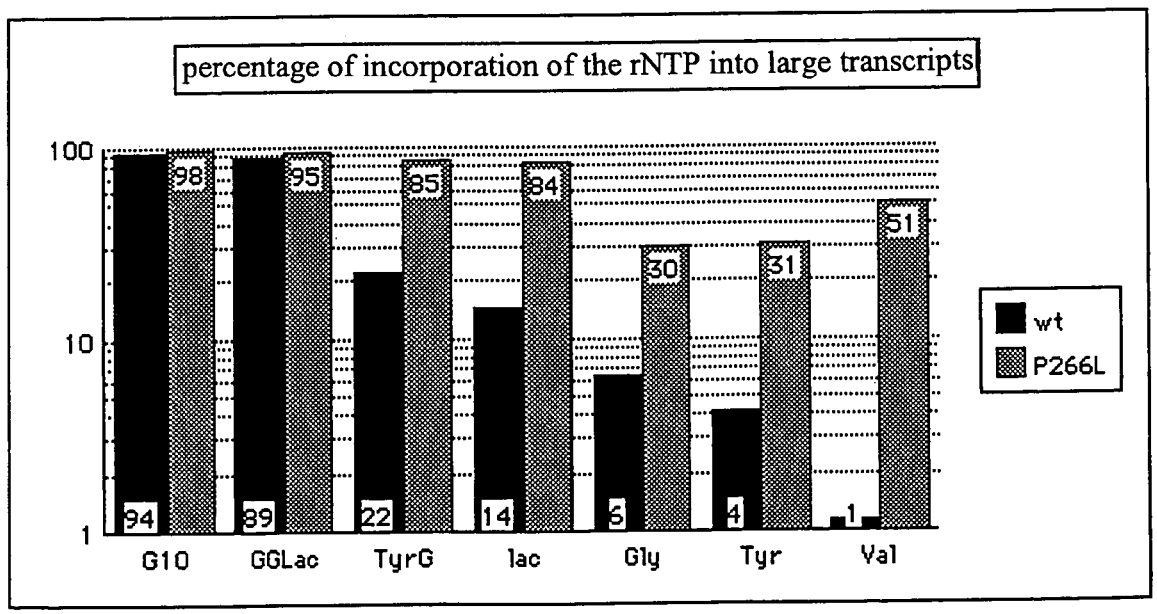

The immediate consequence is summarized in FIG. 8 which includes the results referred to previously, providing figures comparing the productivities of the two polymerases for increasingly unfavourable ITSs. The values indicated correspond to the percentage of incorporation of the rNTP into large transcripts in the case of use of the wild-type T7 polymerase (wt, black columns) and the use of the mutated RNA polymerase SEQ ID NO: 2 (P266L, grey columns).

Apart from G10 and GGLac where the two polymerases give complete satisfaction, in all other cases the wild-type polymerase has a low yield, even a very low yield, comprised between 22% and 1%, whilst that of the mutant remains reasonable, being comprised between 30% and 85%.

BIBLIOGRAPHY

Bonner, G., Lafer, E. M. & Sousa, R. (1994). Characterisation of a set of T7 RNA polymerase active site mutants. J. Biol. Chem. 269, 25120-25128.

Bonner, G., Patra, D., Lafer, E. M. & Sousa, R. (1992). Mutations in T7 RNA polymerase which support the proposal for a common polymerase active site structure. EMBO J. 11, 3767-3775.

Davanloo, P., Rosenberg, A. H., Dunn, J. J. & Studier, F. W. (1984). Cloning and expression of the gene for bacteriophage T7 RNA polymerase. Proc. Natl. Acad. Sci. USA 81, 2035-2039.

Frugier, M., C., F., M. W., H., J-M., L. & R., G. (1994). Synthetic polyamines stimulate in vitro transcription by T7 RNA polymerase. Nucl. Acid Res. 22, 2784-2790.

He, B., Rong, M., Lyakhov, D., Gartenstein, H., Diaz, G., Castagna, R., McAllister, W. T. & Durbin, R. K. (1997). Rapid mutagenesis and purification of phage RNA polymerase. Protein Express Purif. 9.142-151.

Ikeda, R. A. (1992). The efficiency of promoter clearance distinguishes T7 class II and class III promoters. J. Biol. Chem. 267, 11322-11328.

Lapham J, Yu Y T, Shu M D, Steitz J A, Crothers D M.(1997) The position of site-directed cleavage of RNA using RNase H and 2'-O-methyl oligonucleotides is dependent on the enzyme source. RNA 3.950-951

LiZ, Pandit S, Deutscher M P. (1999). Maturation of 23S ribosomal RNA requires the exorbonuclease RNase T. RNA 5.139-146

Lopez, P. J., Guillerez, J., Sousa, R. & Dreyfus, M. (1997). The low processivity of T7 RNA polymerase over the initially transcribed sequence can limit productive initiation in vivo. J. Mol. Biol. 269, 41-51.

Makarova, O. V., Makarov, E. M., Sousa, R. & Dreyfus, M. (1995). Transcribing *Escherichia coli* genes with mutant T7 RNA polymerases: stability of lacZ mRNA inversely correlates with polymerase speed. Proc. Natl. Acad. Sci. USA 92, 12250-12254.

Martin, C. T., Muller, D. K. & Coleman, J. E. (1988). Processivity in early stages of transcription by T7 RNA polymerase. Biochemistry 27, 3966-3974.

Milligan, J. F., Groebe, D. R., Witherell, G. W. & Uhlenbeck, O. C. (1987). Oligonucleotide synthesis using T7 RNA polymerase and synthetic DNA templates. Nucleic Acids Res. 15(21), 8783-8798.

The invention claimed is:

1. A method for producing a RNA of interest, or proteins coded by this RNA of interest, comprising: synthesizing RNA with mutated RNA polymerases of phage origin, the peptide chain of which is modified, with respect to the wild-type RNA polymerases from which they originate, by substitution, or deletion, or addition of at least one amino acid, this modification having the effect of reducing the sensitivity of said RNA polymerases to the initial transcribed sequence (ITS) contained in a DNA sequence coding for an RNA of interest, starting from determined nucleotide sequences comprising a DNA sequence coding for said RNA of interest and the transcription of which is placed under the control of a promoter recognized by the abovementioned wild-type RNA polymerases and mutated RNA polymerases, said method having a production yield of said RNA greater than the yield obtained in the case of use of the wild-type RNA polymerases in the presence of the same non-consensual ITS as that contained in the DNA sequence coding for said RNA of interest, wherein said mutated RNA polymerases are selected from the group consisting of:

those comprising the mutated T7 RNA polymerase represented by SEQ ID NO: 2, comprising a leucine in position 266 substituted for the proline in the wild-type T7 RNA polymerase, or of the proline situated in the homologous position in the wild-type RNA polymerases of other bacteriophages, selected from the group consisting of the proline situated in positions 267 in T3, 289 in KII, and 239 in SP6.

2. A method for producing a RNA of interest, or proteins coded by this RNA of interest, comprising: synthesizing RNA with mutated RNA polymerases of phage origin, the peptide chain of which is modified, with respect to the wild-type RNA polymerases from which they originate, by substitution, or deletion, or addition of at least one amino acid, this modification having the effect of reducing the sensitivity of said RNA polymerases to the ITS contained in a DNA sequence coding for an RNA of interest, starting from determined nucleotide sequences comprising a DNA sequence coding for said RNA of interest and the transcription of which is placed under the control of a promoter recognized by the abovementioned wild-type RNA polymerases and mutated RNA polymerases, said method having a production yield of said RNA greater than the yield obtained in the case of use of the wild-type RNA polymerases in the presence of the same non-consensual ITS as that contained in the DNA sequence coding for said RNA of interest, wherein said mutated RNA polymerases are selected from the group consisting of:

those derived from the wild-type T7 RNA polymerase, and comprising at least one of the following mutations:
replacement of the isoleucine I) in position 117 by a valine (V),
replacement of the isoleucine I) in position 119 by a valine (V),
replacement of the valine (V) in position 134 by an alanine (A),
replacement of the aspartic acid (D) in position 147 by asparagine (N),
replacement of the histidine (H) in position 230 by an arginine (R),
replacement of the proline (P) in position 266 by a leucine (L),
replacement of the arginine (R) in position 291 by a cysteine (C),
said mutated RNA polymerases optionally comprising at least one of the following additional mutations:
replacement of the tyrosine (Y) in position 639 by a phenylalanine (F),
replacement of the isoleucine (I) in position 810 by an asparagine (N),
those derived from the wild-type T3 RNA polymerase, and comprising at least one of the following mutations:
replacement of the aspartic acid (D) in position 148 by asparagine (N),
replacement of the proline (P) in position 267 by a leucine (L),
replacement of the arginine (R) in position 292 by a cysteine (C),
said mutated RNA polymerases optionally comprising at least one of the following additional mutations:
replacement of the tyrosine (Y) in position 640 by a phenylalanine (F),
replacement of the isoleucine (I in position 811 by an asparagine (N),
those derived from the wild-type KII RNA polymerase, and comprising at least one of the following mutations:
replacement of the aspartic acid (D) in position 167 by asparagine (N),
replacement of the proline (P) in position 289 by a leucine (L),
replacement of the arginine (R) in position 314 by a cysteine (C),
said mutated RNA polymerases optionally comprising at least one of the following additional mutations:
replacement of the tyrosine (Y) in position 662 by a phenylalanine (F),
replacement of the isoleucine (I) in position 833 by an asparagine (N), and
those derived from the wild-type SP6 RNA polymerase, and comprising at least one of the following mutations:
replacement of the aspartic acid (D) in position 117 by asparagine (N),
replacement of the proline (P) in position 239 by a leucine (L),
said mutated RNA polymerases optionally comprising at least one of the following additional mutations:
replacement of the tyrosine (Y) in position 631 by a phenylalanine (F),
replacement of the isoleucine (I) in position 804 by an asparagine (N).

3. A method for producing a RNA of interest, or proteins coded by this RNA of interest, comprising: synthesizing RNA with mutated RNA polymerases of phage origin, the peptide chain of which is modified, with respect to the wild-type RNA polymerases from which they originate, by substitution, or deletion, or addition of at least one amino acid, this modification having the effect of reducing the sensitivity of said RNA polymerases to the ITS contained in a DNA sequence coding for an RNA of interest, starting from determined nucleotide sequences comprising a DNA sequence coding for said RNA of interest and the transcription of which is placed under the control of a promoter recognized by the abovementioned wild-type RNA polymerases and mutated RNA polymerases, said method having a production yield of said RNA greater than the yield obtained in the case of use of the wild-type RNA polymerases in the presence of the same non-consensual ITS as that contained in the DNA sequence coding for said RNA of interest, wherein said mutated RNA polymerases are selected from the group consisting of:

the mutated T7 RNA polymerase represented by SEQ ID NO: 2, comprising a leucine in position 266 substituted for the proline, the mutated T7 RNA polymerase represented by SEQ ID NO: 4, comprising a valine in position 117 substituted for the isoleucine, and an alanine in position 134 substituted for the valine, the mutated T7 RNA polymerase represented by SEQ ID NO: 6, comprising a valine in position 119 substituted for the isoleucine, and an asparagine in position 147 substituted for the aspartic acid, the mutated T7 RNA polymerase represented by SEQ ID NO: 8, comprising an arginine in position 230 substituted for the histidine, and a cysteine in position 291 substituted for the arginine, the mutated T7 RNA polymerase represented by SEQ ID NO: 10, comprising a leucine in position 266 substituted for the proline, and a phenylalanine in position 639 substituted for the tyrosine, the mutated T7 RNA polymerase represented by SEQ ID NO: 12, comprising an asparagine in position 810 substituted for the isoleucine, the mutated T7 RNA polymerase represented by SEQ ID NO: 14, comprising a leucine in position 266 substituted for the proline, and an asparagine in position 810 substituted for the isoleucine, and the mutated T7 RNA polymerase represented by SEQ ID NO: 16, comprising a valine in position 119 substituted for the isoleucine, an asparagine in position 147 substituted for the aspartic acid, and an asparagine in position 810 substituted for the isoleucine.

* * * * *

SEQUENCE LISTING

<160> NUMBER OF SEQ ID NOS: 16

<210> SEQ ID NO 1
<211> LENGTH: 2652
<212> TYPE: DNA
<213> ORGANISM: Artificial sequence
<220> FEATURE:
<223> OTHER INFORMATION: Description of the artificial sequence: mutated sequences of bacteriophage T7 RNA polymerase
<220> FEATURE:
<221> NAME/KEY: CDS
<222> LOCATION: (1)..(2652)

<400> SEQUENCE: 1

```
atg aac acg att aac atc gct aag aac gac ttc tct gac atc gaa ctg     48
Met Asn Thr Ile Asn Ile Ala Lys Asn Asp Phe Ser Asp Ile Glu Leu
1               5                   10                  15 gct gct atc ccg ttc aac act ctg gct gac cat tac ggt gag cgt tta     96
Ala Ala Ile Pro Phe Asn Thr Leu Ala Asp His Tyr Gly Glu Arg Leu
            20                  25                  30 gct cgc gaa cag ttg gcc ctt gag cat gag tct tac gag atg ggt gaa    144
Ala Arg Glu Gln Leu Ala Leu Glu His Glu Ser Tyr Glu Met Gly Glu
        35                  40                  45 gca cgc ttc cgc aag atg ttt gag cgt caa ctt aaa gct ggt gag gtt    192
Ala Arg Phe Arg Lys Met Phe Glu Arg Gln Leu Lys Ala Gly Glu Val
    50                  55                  60 gcg gat aac gct gcc gcc aag cct ctc atc act acc cta ctc cct aag    240
Ala Asp Asn Ala Ala Ala Lys Pro Leu Ile Thr Thr Leu Leu Pro Lys
65                  70                  75                  80 atg att gca cgc atc aac gac tgg ttt gag gaa gtg aaa gct aag cgc    288
Met Ile Ala Arg Ile Asn Asp Trp Phe Glu Glu Val Lys Ala Lys Arg
                85                  90                  95 ggc aag cgc ccg aca gcc ttc cag ttc ctg caa gaa atc aag ccg gaa    336
Gly Lys Arg Pro Thr Ala Phe Gln Phe Leu Gln Glu Ile Lys Pro Glu
            100                 105                 110 gcc gta gcg tac atc acc att aag acc act ctg gct tgc cta acc agt    384
Ala Val Ala Tyr Ile Thr Ile Lys Thr Thr Leu Ala Cys Leu Thr Ser
        115                 120                 125 gct gac aat aca acc gtt cag gct gta gca agc gca atc ggt cgg gcc    432
Ala Asp Asn Thr Thr Val Gln Ala Val Ala Ser Ala Ile Gly Arg Ala
    130                 135                 140 att gag gac gag gct cgc ttc ggt cgt atc cgt gac ctt gaa gct aag    480
Ile Glu Asp Glu Ala Arg Phe Gly Arg Ile Arg Asp Leu Glu Ala Lys
145                 150                 155                 160 cac ttc aag aaa aac gtt gag gaa caa ctc aac aag cgc gta ggg cac    528
His Phe Lys Lys Asn Val Glu Glu Gln Leu Asn Lys Arg Val Gly His
                165                 170                 175 gtc tac aag aaa gca ttt atg caa gtt gtc gag gct gac atg ctc tct    576
Val Tyr Lys Lys Ala Phe Met Gln Val Val Glu Ala Asp Met Leu Ser
            180                 185                 190 aag ggt cta ctc ggt ggc gag gcg tgg tct tcg tgg cat aag gaa gac    624
Lys Gly Leu Leu Gly Gly Glu Ala Trp Ser Ser Trp His Lys Glu Asp
        195                 200                 205 tct att cat gta gga gta cgc tgc atc gag atg ctc att gag tca acc    672
Ser Ile His Val Gly Val Arg Cys Ile Glu Met Leu Ile Glu Ser Thr
    210                 215                 220 gga atg gtt agc tta cac cgc caa aat gct ggc gta gta ggt caa gac    720
Gly Met Val Ser Leu His Arg Gln Asn Ala Gly Val Val Gly Gln Asp
225                 230                 235                 240 tct gag act atc gaa ctc gca cct gaa tac gct gag gct atc gca acc    768
```

```
                Ser Glu Thr Ile Glu Leu Ala Pro Glu Tyr Ala Glu Ala Ile Ala Thr
                                245                 250                 255 cgt gca ggt gcg ctg gct ggc atc tct ctg atg ttc caa cct tgc gta         816
Arg Ala Gly Ala Leu Ala Gly Ile Ser Leu Met Phe Gln Pro Cys Val
                260                 265                 270 gtt cct cct aag ccg tgg act ggc att act ggt ggt ggc tat tgg gct         864
Val Pro Pro Lys Pro Trp Thr Gly Ile Thr Gly Gly Gly Tyr Trp Ala
                275                 280                 285 aac ggt cgt cgt cct ctg gcg ctg gtg cgt act cac agt aag aaa gca         912
Asn Gly Arg Arg Pro Leu Ala Leu Val Arg Thr His Ser Lys Lys Ala
        290                 295                 300 ctg atg cgc tac gaa gac gtt tac atg cct gag gtg tac aaa gcg att         960
Leu Met Arg Tyr Glu Asp Val Tyr Met Pro Glu Val Tyr Lys Ala Ile
305                 310                 315                 320 aac att gcg caa aac acc gca tgg aaa atc aac aag aaa gtc cta gcg         1008
Asn Ile Ala Gln Asn Thr Ala Trp Lys Ile Asn Lys Lys Val Leu Ala
                325                 330                 335 gtc gcc aac gta atc acc aag tgg aag cat tgt ccg gtc gag gac atc         1056
Val Ala Asn Val Ile Thr Lys Trp Lys His Cys Pro Val Glu Asp Ile
                340                 345                 350 cct gcg att gag cgt gaa gaa ctc ccg atg aaa ccg gaa gac atc gac         1104
Pro Ala Ile Glu Arg Glu Glu Leu Pro Met Lys Pro Glu Asp Ile Asp
        355                 360                 365 atg aat cct gag gct ctc acc gcg tgg aaa cgt gct gcc gct gct gtg         1152
Met Asn Pro Glu Ala Leu Thr Ala Trp Lys Arg Ala Ala Ala Ala Val
        370                 375                 380 tac cgc aag gac aag gct cgc aag tct cgc cgt atc agc ctt gag ttc         1200
Tyr Arg Lys Asp Lys Ala Arg Lys Ser Arg Arg Ile Ser Leu Glu Phe
385                 390                 395                 400 atg ctt gag caa gcc aat aag ttt gct aac cat aag gcc atc tgg ttc         1248
Met Leu Glu Gln Ala Asn Lys Phe Ala Asn His Lys Ala Ile Trp Phe
                405                 410                 415 cct tac aac atg gac tgg cgc ggt cgt gtt tac gct gtg tca atg ttc         1296
Pro Tyr Asn Met Asp Trp Arg Gly Arg Val Tyr Ala Val Ser Met Phe
                420                 425                 430 aac ccg caa ggt aac gat atg acc aaa gga ctg ctt acg ctg gcg aaa         1344
Asn Pro Gln Gly Asn Asp Met Thr Lys Gly Leu Leu Thr Leu Ala Lys
                435                 440                 445 ggt aaa cca atc ggt aag gaa ggt tac tac tgg ctg aaa atc cac ggt         1392
Gly Lys Pro Ile Gly Lys Glu Gly Tyr Tyr Trp Leu Lys Ile His Gly
        450                 455                 460 gca aac tgt gcg ggt gtc gat aag gtt ccg ttc cct gag cgc atc aag         1440
Ala Asn Cys Ala Gly Val Asp Lys Val Pro Phe Pro Glu Arg Ile Lys
465                 470                 475                 480 ttc att gag gaa aac cac gag aac atc atg gct tgc gct aag tct cca         1488
Phe Ile Glu Glu Asn His Glu Asn Ile Met Ala Cys Ala Lys Ser Pro
                485                 490                 495 ctg gag aac act tgg tgg gct gag caa gat tct ccg ttc tgc ttc ctt         1536
Leu Glu Asn Thr Trp Trp Ala Glu Gln Asp Ser Pro Phe Cys Phe Leu
                500                 505                 510 gcg ttc tgc ttt gag tac gct ggg gta cag cac cac ggc ctg agc tat         1584
Ala Phe Cys Phe Glu Tyr Ala Gly Val Gln His His Gly Leu Ser Tyr
                515                 520                 525 aac tgc tcc ctt ccg ctg gcg ttt gac ggg tct tgc tct ggc atc cag         1632
Asn Cys Ser Leu Pro Leu Ala Phe Asp Gly Ser Cys Ser Gly Ile Gln
        530                 535                 540 cac ttc tcc gcg atg ctc cga gat gag gta ggt ggt cgc gcg gtt aac         1680
His Phe Ser Ala Met Leu Arg Asp Glu Val Gly Gly Arg Ala Val Asn
545                 550                 555                 560
```

```
ttg ctt cct agt gaa acc gtt cag gac atc tac ggg att gtt gct aag      1728
Leu Leu Pro Ser Glu Thr Val Gln Asp Ile Tyr Gly Ile Val Ala Lys
            565                 570                 575 aaa gtc aac gag att cta caa gca gac gca atc aat ggg acc gat aac      1776
Lys Val Asn Glu Ile Leu Gln Ala Asp Ala Ile Asn Gly Thr Asp Asn
580                 585                 590 gaa gta gtt acc gtg acc gat gag aac act ggt gaa atc tct gag aaa      1824
Glu Val Val Thr Val Thr Asp Glu Asn Thr Gly Glu Ile Ser Glu Lys
                595                 600                 605 gtc aag ctg ggc act aag gca ctg gct ggt caa tgg ctg gct tac ggt      1872
Val Lys Leu Gly Thr Lys Ala Leu Ala Gly Gln Trp Leu Ala Tyr Gly
    610                 615                 620 gtt act cgc agt gtg act aag cgt tca gtc atg acg ctg gct tac ggg      1920
Val Thr Arg Ser Val Thr Lys Arg Ser Val Met Thr Leu Ala Tyr Gly
625                 630                 635                 640 tcc aaa gag ttc ggc ttc cgt caa caa gtg ctg gaa gat acc att cag      1968
Ser Lys Glu Phe Gly Phe Arg Gln Gln Val Leu Glu Asp Thr Ile Gln
                645                 650                 655 cca gct att gat tcc ggc aag ggt ctg atg ttc act cag ccg aat cag      2016
Pro Ala Ile Asp Ser Gly Lys Gly Leu Met Phe Thr Gln Pro Asn Gln
    660                 665                 670 gct gct gga tac atg gct aag ctg att tgg gaa tct gtg agc gtg acg      2064
Ala Ala Gly Tyr Met Ala Lys Leu Ile Trp Glu Ser Val Ser Val Thr
675                 680                 685 gtg gta gct gcg gtt gaa gca atg aac tgg ctt aag tct gct gct aag      2112
Val Val Ala Ala Val Glu Ala Met Asn Trp Leu Lys Ser Ala Ala Lys
                690                 695                 700 ctg ctg gct gct gag gtc aaa gat aag aag act gga gag att ctt cgc      2160
Leu Leu Ala Ala Glu Val Lys Asp Lys Lys Thr Gly Glu Ile Leu Arg
705                 710                 715                 720 aag cgt tgc gct gtg cat tgg gta act cct gat ggt ttc cct gtg tgg      2208
Lys Arg Cys Ala Val His Trp Val Thr Pro Asp Gly Phe Pro Val Trp
                725                 730                 735 cag gaa tac aag aag cct att cag acg cgc ttg aac ctg atg ttc ctc      2256
Gln Glu Tyr Lys Lys Pro Ile Gln Thr Arg Leu Asn Leu Met Phe Leu
            740                 745                 750 ggt cag ttc cgc tta cag cct acc att aac acc aac aaa gat agc gag      2304
Gly Gln Phe Arg Leu Gln Pro Thr Ile Asn Thr Asn Lys Asp Ser Glu
        755                 760                 765 att gat gca cac aaa cag gag tct ggt atc gct cct aac ttt gta cac      2352
Ile Asp Ala His Lys Gln Glu Ser Gly Ile Ala Pro Asn Phe Val His
770                 775                 780 agc caa gac ggt agc cac ctt cgt aag act gta gtg tgg gca cac gag      2400
Ser Gln Asp Gly Ser His Leu Arg Lys Thr Val Val Trp Ala His Glu
785                 790                 795                 800 aag tac gga atc gaa tct ttt gca ctg att cac gac tcc ttc ggt acc      2448
Lys Tyr Gly Ile Glu Ser Phe Ala Leu Ile His Asp Ser Phe Gly Thr
                805                 810                 815 att ccg gct gac gct gcg aac ctg ttc aaa gca gtg cgc gaa act atg      2496
Ile Pro Ala Asp Ala Ala Asn Leu Phe Lys Ala Val Arg Glu Thr Met
        820                 825                 830 gtt gac aca tat gag tct tgt gat gta ctg gct gat ttc tac gac cag      2544
Val Asp Thr Tyr Glu Ser Cys Asp Val Leu Ala Asp Phe Tyr Asp Gln
            835                 840                 845 ttc gct gac cag ttg cac gag tct caa ttg gac aaa atg cca gca ctt      2592
Phe Ala Asp Gln Leu His Glu Ser Gln Leu Asp Lys Met Pro Ala Leu
850                 855                 860 ccg gct aaa ggt aac ttg aac ctc cgt gac atc tta gag tcg gac ttc      2640
Pro Ala Lys Gly Asn Leu Asn Leu Arg Asp Ile Leu Glu Ser Asp Phe
865                 870                 875                 880
```

```
gcg ttc gcg taa                                                           2652
Ala Phe Ala <210> SEQ ID NO 2
<211> LENGTH: 883
<212> TYPE: PRT
<213> ORGANISM: Artificial sequence
<220> FEATURE:
<223> OTHER INFORMATION: Description of the artificial sequence: mutated
      sequences of bacteriophage T7 RNA polymerase

<400> SEQUENCE: 2

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Leu Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
```

-continued

```
            340             345             350
Pro Ala Ile Glu Arg Glu Leu Pro Met Lys Pro Glu Asp Ile Asp
            355                 360                 365
Met Asn Pro Glu Ala Leu Thr Ala Trp Lys Arg Ala Ala Ala Val
            370                 375                 380
Tyr Arg Lys Asp Lys Ala Arg Lys Ser Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
            420                 425                 430
Asn Pro Gln Gly Asn Asp Met Thr Lys Gly Leu Leu Thr Leu Ala Lys
            435                 440                 445
Gly Lys Pro Ile Gly Lys Glu Gly Tyr Tyr Trp Leu Lys Ile His Gly
            450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
            515                 520                 525
Asn Cys Ser Leu Pro Leu Ala Phe Asp Gly Ser Cys Ser Gly Ile Gln
            530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
            580                 585                 590
Glu Val Val Thr Val Thr Asp Glu Asn Thr Gly Glu Ile Ser Glu Lys
            595                 600                 605
Val Lys Leu Gly Thr Lys Ala Leu Ala Gly Gln Trp Leu Ala Tyr Gly
            610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Val Ser Val Thr
            675                 680                 685
Val Val Ala Ala Val Glu Ala Met Asn Trp Leu Lys Ser Ala Ala Lys
            690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
            755                 760                 765
```

```
Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
                835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 3
<211> LENGTH: 2652
<212> TYPE: DNA
<213> ORGANISM: Artificial sequence
<220> FEATURE:
<223> OTHER INFORMATION: Description of the artificial sequence: mutated
      sequences of bacteriophage T7 RNA polymerase
<220> FEATURE:
<221> NAME/KEY: CDS
<222> LOCATION: (1)..(2652)

<400> SEQUENCE: 3
```

```
atg aac acg att aac atc gct aag aac gac ttc tct gac atc gaa ctg    48
Met Asn Thr Ile Asn Ile Ala Lys Asn Asp Phe Ser Asp Ile Glu Leu
1               5                   10                  15 gct gct atc ccg ttc aac act ctg gct gac cat tac ggt gag cgt tta    96
Ala Ala Ile Pro Phe Asn Thr Leu Ala Asp His Tyr Gly Glu Arg Leu
                20                  25                  30 gct cgc gaa cag ttg gcc ctt gag cat gag tct tac gag atg ggt gaa    144
Ala Arg Glu Gln Leu Ala Leu Glu His Glu Ser Tyr Glu Met Gly Glu
            35                  40                  45 gca cgc ttc cgc aag atg ttt gag cgt caa ctt aaa gct ggt gag gtt    192
Ala Arg Phe Arg Lys Met Phe Glu Arg Gln Leu Lys Ala Gly Glu Val
        50                  55                  60 gcg gat aac gct gcc gcc aag cct ctc atc act acc cta ctc cct aag    240
Ala Asp Asn Ala Ala Ala Lys Pro Leu Ile Thr Thr Leu Leu Pro Lys
65                  70                  75                  80 atg att gca cgc atc aac gac tgg ttt gag gaa gtg aaa gct aag cgc    288
Met Ile Ala Arg Ile Asn Asp Trp Phe Glu Glu Val Lys Ala Lys Arg
                85                  90                  95 ggc aag cgc ccg aca gcc ttc cag ttc ctg caa gaa atc aag ccg gaa    336
Gly Lys Arg Pro Thr Ala Phe Gln Phe Leu Gln Glu Ile Lys Pro Glu
                100                 105                 110 gcc gta gcg tac gtc acc att aag acc act ctg gct tgc cta acc agt    384
Ala Val Ala Tyr Val Thr Ile Lys Thr Thr Leu Ala Cys Leu Thr Ser
            115                 120                 125 gct gac aat aca acc gct cag gct gta gca agc gca atc ggt cgg gcc    432
Ala Asp Asn Thr Thr Ala Gln Ala Val Ala Ser Ala Ile Gly Arg Ala
        130                 135                 140 att gag gac gag gct cgc ttc ggt cgt atc cgt gac ctt gaa gct aag    480
Ile Glu Asp Glu Ala Arg Phe Gly Arg Ile Arg Asp Leu Glu Ala Lys
145                 150                 155                 160 cac ttc aag aaa aac gtt gag gaa caa ctc aac aag cgc gta ggg cac    528
```

```
His Phe Lys Lys Asn Val Glu Glu Gln Leu Asn Lys Arg Val Gly His
            165                 170                 175 gtc tac aag aaa gca ttt atg caa gtt gtc gag gct gac atg ctc tct         576
Val Tyr Lys Lys Ala Phe Met Gln Val Val Glu Ala Asp Met Leu Ser
            180                 185                 190 aag ggt cta ctc ggt ggc gag gcg tgg tct tcg tgg cat aag gaa gac         624
Lys Gly Leu Leu Gly Gly Glu Ala Trp Ser Ser Trp His Lys Glu Asp
            195                 200                 205 tct att cat gta gga gta cgc tgc atc gag atg ctc att gag tca acc         672
Ser Ile His Val Gly Val Arg Cys Ile Glu Met Leu Ile Glu Ser Thr
            210                 215                 220 gga atg gtt agc tta cac cgc caa aat gct ggc gta gta ggt caa gac         720
Gly Met Val Ser Leu His Arg Gln Asn Ala Gly Val Val Gly Gln Asp
225                 230                 235                 240 tct gag act atc gaa ctc gca cct gaa tac gct gag gct atc gca acc         768
Ser Glu Thr Ile Glu Leu Ala Pro Glu Tyr Ala Glu Ala Ile Ala Thr
                245                 250                 255 cgt gca ggt gcg ctg gct ggc atc tct ccg atg ttc caa cct tgc gta         816
Arg Ala Gly Ala Leu Ala Gly Ile Ser Pro Met Phe Gln Pro Cys Val
                260                 265                 270 gtt cct cct aag ccg tgg act ggc att act ggt ggc ggc tat tgg gct         864
Val Pro Pro Lys Pro Trp Thr Gly Ile Thr Gly Gly Gly Tyr Trp Ala
                275                 280                 285 aac ggt cgt cgt cct ctg gcg ctg gtg cgt act cac agt aag aaa gca         912
Asn Gly Arg Arg Pro Leu Ala Leu Val Arg Thr His Ser Lys Lys Ala
            290                 295                 300 ctg atg cgc tac gaa gac gtt tac atg cct gag gtg tac aaa gcg att         960
Leu Met Arg Tyr Glu Asp Val Tyr Met Pro Glu Val Tyr Lys Ala Ile
305                 310                 315                 320 aac att gcg caa aac acc gca tgg aaa atc aac aag aaa gtc cta gcg        1008
Asn Ile Ala Gln Asn Thr Ala Trp Lys Ile Asn Lys Lys Val Leu Ala
                325                 330                 335 gtc gcc aac gta atc acc aag tgg aag cat tgt ccg gtc gag gac atc        1056
Val Ala Asn Val Ile Thr Lys Trp Lys His Cys Pro Val Glu Asp Ile
                340                 345                 350 cct gcg att gag cgt gaa gaa ctc ccg atg aaa ccg gaa gac atc gac        1104
Pro Ala Ile Glu Arg Glu Glu Leu Pro Met Lys Pro Glu Asp Ile Asp
                355                 360                 365 atg aat cct gag gct ctc acc gcg tgg aaa cgt gct gcc gct gct gtg        1152
Met Asn Pro Glu Ala Leu Thr Ala Trp Lys Arg Ala Ala Ala Ala Val
                370                 375                 380 tac cgc aag gac aag gct cgc aag tct cgc cgt atc agc ctt gag ttc        1200
Tyr Arg Lys Asp Lys Ala Arg Lys Ser Arg Arg Ile Ser Leu Glu Phe
385                 390                 395                 400 atg ctt gag caa gcc aat aag ttt gct aac cat aag gcc atc tgg ttc        1248
Met Leu Glu Gln Ala Asn Lys Phe Ala Asn His Lys Ala Ile Trp Phe
                405                 410                 415 cct tac aac atg gac tgg cgc ggt cgt gtt tac gct gtg tca atg ttc        1296
Pro Tyr Asn Met Asp Trp Arg Gly Arg Val Tyr Ala Val Ser Met Phe
                420                 425                 430 aac ccg caa ggt aac gat atg acc aaa gga ctg ctt acg ctg gcg aaa        1344
Asn Pro Gln Gly Asn Asp Met Thr Lys Gly Leu Leu Thr Leu Ala Lys
                435                 440                 445 ggt aaa cca atc ggt aag gaa ggt tac tac tgg ctg aaa atc cac ggt        1392
Gly Lys Pro Ile Gly Lys Glu Gly Tyr Tyr Trp Leu Lys Ile His Gly
            450                 455                 460 gca aac tgt gcg ggt gtc gat aag gtt ccg ttc cct gag cgc atc aag        1440
Ala Asn Cys Ala Gly Val Asp Lys Val Pro Phe Pro Glu Arg Ile Lys
465                 470                 475                 480
```

```
ttc att gag gaa aac cac gag aac atc atg gct tgc gct aag tct cca    1488
Phe Ile Glu Glu Asn His Glu Asn Ile Met Ala Cys Ala Lys Ser Pro
                485                 490                 495 ctg gag aac act tgg tgg gct gag caa gat tct ccg ttc tgc ttc ctt    1536
Leu Glu Asn Thr Trp Trp Ala Glu Gln Asp Ser Pro Phe Cys Phe Leu
            500                 505                 510 gcg ttc tgc ttt gag tac gct ggg gta cag cac cac ggc ctg agc tat    1584
Ala Phe Cys Phe Glu Tyr Ala Gly Val Gln His His Gly Leu Ser Tyr
        515                 520                 525 aac tgc tcc ctt ccg ctg gcg ttt gac ggg tct tgc tct ggc atc cag    1632
Asn Cys Ser Leu Pro Leu Ala Phe Asp Gly Ser Cys Ser Gly Ile Gln
    530                 535                 540 cac ttc tcc gcg atg ctc cga gat gag gta ggt ggt cgc gcg gtt aac    1680
His Phe Ser Ala Met Leu Arg Asp Glu Val Gly Gly Arg Ala Val Asn
545                 550                 555                 560 ttg ctt cct agt gaa acc gtt cag gac atc tac ggg att gtt gct aag    1728
Leu Leu Pro Ser Glu Thr Val Gln Asp Ile Tyr Gly Ile Val Ala Lys
                565                 570                 575 aaa gtc aac gag att cta caa gca gac gca atc aat ggg acc gat aac    1776
Lys Val Asn Glu Ile Leu Gln Ala Asp Ala Ile Asn Gly Thr Asp Asn
            580                 585                 590 gaa gta gtt acc gtg acc gat gag aac act ggt gaa atc tct gag aaa    1824
Glu Val Val Thr Val Thr Asp Glu Asn Thr Gly Glu Ile Ser Glu Lys
        595                 600                 605 gtc aag ctg ggc act aag gca ctg gct ggt caa tgg ctg gct tac ggt    1872
Val Lys Leu Gly Thr Lys Ala Leu Ala Gly Gln Trp Leu Ala Tyr Gly
    610                 615                 620 gtt act cgc agt gtg act aag cgt tca gtc atg acg ctg gct tac ggg    1920
Val Thr Arg Ser Val Thr Lys Arg Ser Val Met Thr Leu Ala Tyr Gly
625                 630                 635                 640 tcc aaa gag ttc ggc ttc cgt caa caa gtg ctg gaa gat acc att cag    1968
Ser Lys Glu Phe Gly Phe Arg Gln Gln Val Leu Glu Asp Thr Ile Gln
                645                 650                 655 cca gct att gat tcc ggc aag ggt ctg atg ttc act cag ccg aat cag    2016
Pro Ala Ile Asp Ser Gly Lys Gly Leu Met Phe Thr Gln Pro Asn Gln
            660                 665                 670 gct gct gga tac atg gct aag ctg att tgg gaa tct gtg agc gtg acg    2064
Ala Ala Gly Tyr Met Ala Lys Leu Ile Trp Glu Ser Val Ser Val Thr
        675                 680                 685 gtg gta gct gcg gtt gaa gca atg aac tgg ctt aag tct gct gct aag    2112
Val Val Ala Ala Val Glu Ala Met Asn Trp Leu Lys Ser Ala Ala Lys
    690                 695                 700 ctg ctg gct gct gag gtc aaa gat aag aag act gga gag att ctt cgc    2160
Leu Leu Ala Ala Glu Val Lys Asp Lys Lys Thr Gly Glu Ile Leu Arg
705                 710                 715                 720 aag cgt tgc gct gtg cat tgg gta act cct gat ggt ttc cct gtg tgg    2208
Lys Arg Cys Ala Val His Trp Val Thr Pro Asp Gly Phe Pro Val Trp
                725                 730                 735 cag gaa tac aag aag cct att cag acg cgc ttg aac ctg atg ttc ctc    2256
Gln Glu Tyr Lys Lys Pro Ile Gln Thr Arg Leu Asn Leu Met Phe Leu
            740                 745                 750 ggt cag ttc cgc tta cag cct acc att aac acc aac aaa gat agc gag    2304
Gly Gln Phe Arg Leu Gln Pro Thr Ile Asn Thr Asn Lys Asp Ser Glu
        755                 760                 765 att gat gca cac aaa cag gag tct ggt atc gct cct aac ttt gta cac    2352
Ile Asp Ala His Lys Gln Glu Ser Gly Ile Ala Pro Asn Phe Val His
    770                 775                 780 agc caa gac ggt agc cac ctt cgt aag act gta gtg tgg gca cac gag    2400
Ser Gln Asp Gly Ser His Leu Arg Lys Thr Val Val Trp Ala His Glu
785                 790                 795                 800
```

```
aag tac gga atc gaa tct ttt gca ctg att cac gac tcc ttc ggt acc       2448
Lys Tyr Gly Ile Glu Ser Phe Ala Leu Ile His Asp Ser Phe Gly Thr
            805                 810                 815 att ccg gct gac gct gcg aac ctg ttc aaa gca gtg cgc gaa act atg       2496
Ile Pro Ala Asp Ala Ala Asn Leu Phe Lys Ala Val Arg Glu Thr Met
        820                 825                 830 gtt gac aca tat gag tct tgt gat gta ctg gct gat ttc tac gac cag       2544
Val Asp Thr Tyr Glu Ser Cys Asp Val Leu Ala Asp Phe Tyr Asp Gln
835                 840                 845 ttc gct gac cag ttg cac gag tct caa ttg gac aaa atg cca gca ctt       2592
Phe Ala Asp Gln Leu His Glu Ser Gln Leu Asp Lys Met Pro Ala Leu
    850                 855                 860 ccg gct aaa ggt aac ttg aac ctc cgt gac atc tta gag tcg gac ttc       2640
Pro Ala Lys Gly Asn Leu Asn Leu Arg Asp Ile Leu Glu Ser Asp Phe
865                 870                 875                 880 gcg ttc gcg taa                                                       2652
Ala Phe Ala
```

<210> SEQ ID NO 4
<211> LENGTH: 883
<212> TYPE: PRT
<213> ORGANISM: Artificial sequence
<220> FEATURE:
<223> OTHER INFORMATION: Description of the artificial sequence: mutated
      sequences of bacteriophage T7 RNA polymerase

<400> SEQUENCE: 4

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Val Thr Ile Lys Thr Thr Leu Ala Cys Leu Thr Ser
        115                 120                 125

Ala Asp Asn Thr Thr Ala Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240
```

```
Ser Glu Thr Ile Glu Leu Ala Pro Tyr Ala Glu Ala Ile Ala Thr
            245                 250                 255

Arg Ala Gly Ala Leu Ala Gly Ile Ser Pro Met Phe Gln Pro Cys Val
        260                 265                 270

Val Pro Pro Lys Pro Trp Thr Gly Ile Thr Gly Gly Tyr Trp Ala
            275                 280             285

Asn Gly Arg Arg Pro Leu Ala Leu Val Arg Thr His Ser Lys Lys Ala
        290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
        580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
        610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655
```

```
Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
        690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 5
<211> LENGTH: 2652
<212> TYPE: DNA
<213> ORGANISM: Artificial sequence
<220> FEATURE:
<223> OTHER INFORMATION: Description of the artificial sequence: mutated
      sequences of bacteriophage T7 RNA polymerase
<220> FEATURE:
<221> NAME/KEY: CDS
<222> LOCATION: (1)..(2652)

<400> SEQUENCE: 5 atg aac acg att aac atc gct aag aac gac ttc tct gac atc gaa ctg     48
Met Asn Thr Ile Asn Ile Ala Lys Asn Asp Phe Ser Asp Ile Glu Leu
1               5                   10                  15 gct gct atc ccg ttc aac act ctg gct gac cat tac ggt gag cgt tta     96
Ala Ala Ile Pro Phe Asn Thr Leu Ala Asp His Tyr Gly Glu Arg Leu
            20                  25                  30 gct cgc gaa cag ttg gcc ctt gag cat gag tct tac gag atg ggt gaa    144
Ala Arg Glu Gln Leu Ala Leu Glu His Glu Ser Tyr Glu Met Gly Glu
        35                  40                  45 gca cgc ttc cgc aag atg ttt gag cgt caa ctt aaa gct ggt gag gtt    192
Ala Arg Phe Arg Lys Met Phe Glu Arg Gln Leu Lys Ala Gly Glu Val
    50                  55                  60 gcg gat aac gct gcc gcc aag cct ctc atc act acc cta ctc cct aag    240
Ala Asp Asn Ala Ala Ala Lys Pro Leu Ile Thr Thr Leu Leu Pro Lys
65                  70                  75                  80 atg att gca cgc atc aac gac tgg ttt gag gaa gtg aaa gct aag cgc    288
```

```
Met Ile Ala Arg Ile Asn Asp Trp Phe Glu Glu Val Lys Ala Lys Arg
                85                   90                  95 ggc aag cgc ccg aca gcc ttc cag ttc ctg caa gaa atc aag ccg gaa          336
Gly Lys Arg Pro Thr Ala Phe Gln Phe Leu Gln Glu Ile Lys Pro Glu
            100                 105                 110 gcc gta gcg tac atc acc gtt aag acc act ctg gct tgc cta acc agt          384
Ala Val Ala Tyr Ile Thr Val Lys Thr Thr Leu Ala Cys Leu Thr Ser
            115                 120                 125 gct gac aat aca acc gtt cag gct gta gca agc gca atc ggt cgg gcc          432
Ala Asp Asn Thr Thr Val Gln Ala Val Ala Ser Ala Ile Gly Arg Ala
    130                 135                 140 att gag aac gag gct cgc ttc ggt cgt atc cgt gac ctt gaa gct aag          480
Ile Glu Asn Glu Ala Arg Phe Gly Arg Ile Arg Asp Leu Glu Ala Lys
145                 150                 155                 160 cac ttc aag aaa aac gtt gag gaa caa ctc aac aag cgc gta ggg cac          528
His Phe Lys Lys Asn Val Glu Glu Gln Leu Asn Lys Arg Val Gly His
                165                 170                 175 gtc tac aag aaa gca ttt atg caa gtt gtc gag gct gac atg ctc tct          576
Val Tyr Lys Lys Ala Phe Met Gln Val Val Glu Ala Asp Met Leu Ser
            180                 185                 190 aag ggt cta ctc ggt ggc gag gcg tgg tct tcg tgg cat aag gaa gac          624
Lys Gly Leu Leu Gly Gly Glu Ala Trp Ser Ser Trp His Lys Glu Asp
        195                 200                 205 tct att cat gta gga gta cgc tgc atc gag atg ctc att gag tca acc          672
Ser Ile His Val Gly Val Arg Cys Ile Glu Met Leu Ile Glu Ser Thr
    210                 215                 220 gga atg gtt agc tta cac cgc caa aat gct ggc gta gta ggt caa gac          720
Gly Met Val Ser Leu His Arg Gln Asn Ala Gly Val Val Gly Gln Asp
225                 230                 235                 240 tct gag act atc gaa ctc gca cct gaa tac gct gag gct atc gca acc          768
Ser Glu Thr Ile Glu Leu Ala Pro Glu Tyr Ala Glu Ala Ile Ala Thr
                245                 250                 255 cgt gca ggt gcg ctg gct ggc atc tct ccg atg ttc caa cct tgc gta          816
Arg Ala Gly Ala Leu Ala Gly Ile Ser Pro Met Phe Gln Pro Cys Val
            260                 265                 270 gtt cct cct aag ccg tgg act ggc att act ggt ggt ggc tat tgg gct          864
Val Pro Pro Lys Pro Trp Thr Gly Ile Thr Gly Gly Gly Tyr Trp Ala
        275                 280                 285 aac ggt cgt cgt cct ctg gcg ctg gtg cgt act cac agt aag aaa gca          912
Asn Gly Arg Arg Pro Leu Ala Leu Val Arg Thr His Ser Lys Lys Ala
    290                 295                 300 ctg atg cgc tac gaa gac gtt tac atg cct gag gtg tac aaa gcg att          960
Leu Met Arg Tyr Glu Asp Val Tyr Met Pro Glu Val Tyr Lys Ala Ile
305                 310                 315                 320 aac att gcg caa aac acc gca tgg aaa atc aac aag aaa gtc cta gcg         1008
Asn Ile Ala Gln Asn Thr Ala Trp Lys Ile Asn Lys Lys Val Leu Ala
                325                 330                 335 gtc gcc aac gta atc acc aag tgg aag cat tgt ccg gtc gag gac atc         1056
Val Ala Asn Val Ile Thr Lys Trp Lys His Cys Pro Val Glu Asp Ile
            340                 345                 350 cct gcg att gag cgt gaa gaa ctc ccg atg aaa ccg gaa gac atc gac         1104
Pro Ala Ile Glu Arg Glu Glu Leu Pro Met Lys Pro Glu Asp Ile Asp
        355                 360                 365 atg aat cct gag gct ctc acc gcg tgg aaa cgt gct gcc gct gct gtg         1152
Met Asn Pro Glu Ala Leu Thr Ala Trp Lys Arg Ala Ala Ala Ala Val
    370                 375                 380 tac cgc aag gac aag gct cgc aag tct cgc cgt atc agc ctt gag ttc         1200
Tyr Arg Lys Asp Lys Ala Arg Lys Ser Arg Arg Ile Ser Leu Glu Phe
385                 390                 395                 400
```

```
atg ctt gag caa gcc aat aag ttt gct aac cat aag gcc atc tgg ttc     1248
Met Leu Glu Gln Ala Asn Lys Phe Ala Asn His Lys Ala Ile Trp Phe
            405                 410                 415 cct tac aac atg gac tgg cgc ggt cgt gtt tac gct gtg tca atg ttc     1296
Pro Tyr Asn Met Asp Trp Arg Gly Arg Val Tyr Ala Val Ser Met Phe
        420                 425                 430 aac ccg caa ggt aac gat atg acc aaa gga ctg ctt acg ctg gcg aaa     1344
Asn Pro Gln Gly Asn Asp Met Thr Lys Gly Leu Leu Thr Leu Ala Lys
    435                 440                 445 ggt aaa cca atc ggt aag gaa ggt tac tac tgg ctg aaa atc cac ggt     1392
Gly Lys Pro Ile Gly Lys Glu Gly Tyr Tyr Trp Leu Lys Ile His Gly
450                 455                 460 gca aac tgt gcg ggt gtc gat aag gtt ccg ttc cct gag cgc atc aag     1440
Ala Asn Cys Ala Gly Val Asp Lys Val Pro Phe Pro Glu Arg Ile Lys
465                 470                 475                 480 ttc att gag gaa aac cac gag aac atc atg gct tgc gct aag tct cca     1488
Phe Ile Glu Glu Asn His Glu Asn Ile Met Ala Cys Ala Lys Ser Pro
                485                 490                 495 ctg gag aac act tgg tgg gct gag caa gat tct ccg ttc tgc ttc ctt     1536
Leu Glu Asn Thr Trp Trp Ala Glu Gln Asp Ser Pro Phe Cys Phe Leu
            500                 505                 510 gcg ttc tgc ttt gag tac gct ggg gta cag cac cac ggc ctg agc tat     1584
Ala Phe Cys Phe Glu Tyr Ala Gly Val Gln His His Gly Leu Ser Tyr
        515                 520                 525 aac tgc tcc ctt ccg ctg gcg ttt gac ggg tct tgc tct ggc atc cag     1632
Asn Cys Ser Leu Pro Leu Ala Phe Asp Gly Ser Cys Ser Gly Ile Gln
    530                 535                 540 cac ttc tcc gcg atg ctc cga gat gag gta ggt ggt cgc gcg gtt aac     1680
His Phe Ser Ala Met Leu Arg Asp Glu Val Gly Gly Arg Ala Val Asn
545                 550                 555                 560 ttg ctt cct agt gaa acc gtt cag gac atc tac ggg att gtt gct aag     1728
Leu Leu Pro Ser Glu Thr Val Gln Asp Ile Tyr Gly Ile Val Ala Lys
                565                 570                 575 aaa gtc aac gag att cta caa gca gac gca atc aat ggg acc gat aac     1776
Lys Val Asn Glu Ile Leu Gln Ala Asp Ala Ile Asn Gly Thr Asp Asn
            580                 585                 590 gaa gta gtt acc gtg acc gat gag aac act ggt gaa atc tct gag aaa     1824
Glu Val Val Thr Val Thr Asp Glu Asn Thr Gly Glu Ile Ser Glu Lys
        595                 600                 605 gtc aag ctg ggc act aag gca ctg gct ggt caa tgg ctg gct tac ggt     1872
Val Lys Leu Gly Thr Lys Ala Leu Ala Gly Gln Trp Leu Ala Tyr Gly
    610                 615                 620 gtt act cgc agt gtg act aag cgt tca gtc atg acg ctg gct tac ggg     1920
Val Thr Arg Ser Val Thr Lys Arg Ser Val Met Thr Leu Ala Tyr Gly
625                 630                 635                 640 tcc aaa gag ttc ggc ttc cgt caa caa gtg ctg gaa gat acc att cag     1968
Ser Lys Glu Phe Gly Phe Arg Gln Gln Val Leu Glu Asp Thr Ile Gln
                645                 650                 655 cca gct att gat tcc ggc aag ggt ctg atg ttc act cag ccg aat cag     2016
Pro Ala Ile Asp Ser Gly Lys Gly Leu Met Phe Thr Gln Pro Asn Gln
            660                 665                 670 gct gct gga tac atg gct aag ctg att tgg gaa tct gtg agc gtg acg     2064
Ala Ala Gly Tyr Met Ala Lys Leu Ile Trp Glu Ser Val Ser Val Thr
        675                 680                 685 gtg gta gct gcg gtt gaa gca atg aac tgg ctt aag tct gct gct aag     2112
Val Val Ala Ala Val Glu Ala Met Asn Trp Leu Lys Ser Ala Ala Lys
    690                 695                 700 ctg ctg gct gct gag gtc aaa gat aag aag act gga gag att ctt cgc     2160
Leu Leu Ala Ala Glu Val Lys Asp Lys Lys Thr Gly Glu Ile Leu Arg
705                 710                 715                 720
```

-continued

```
aag cgt tgc gct gtg cat tgg gta act cct gat ggt ttc cct gtg tgg      2208
Lys Arg Cys Ala Val His Trp Val Thr Pro Asp Gly Phe Pro Val Trp
            725                 730                 735 cag gaa tac aag aag cct att cag acg cgc ttg aac ctg atg ttc ctc      2256
Gln Glu Tyr Lys Lys Pro Ile Gln Thr Arg Leu Asn Leu Met Phe Leu
        740                 745                 750 ggt cag ttc cgc tta cag cct acc att aac acc aac aaa gat agc gag      2304
Gly Gln Phe Arg Leu Gln Pro Thr Ile Asn Thr Asn Lys Asp Ser Glu
    755                 760                 765 att gat gca cac aaa cag gag tct ggt atc gct cct aac ttt gta cac      2352
Ile Asp Ala His Lys Gln Glu Ser Gly Ile Ala Pro Asn Phe Val His
770                 775                 780 agc caa gac ggt agc cac ctt cgt aag act gta gtg tgg gca cac gag      2400
Ser Gln Asp Gly Ser His Leu Arg Lys Thr Val Val Trp Ala His Glu
785                 790                 795                 800 aag tac gga atc gaa tct ttt gca ctg att cac gac tcc ttc ggt acc      2448
Lys Tyr Gly Ile Glu Ser Phe Ala Leu Ile His Asp Ser Phe Gly Thr
                805                 810                 815 att ccg gct gac gct gcg aac ctg ttc aaa gca gtg cgc gaa act atg      2496
Ile Pro Ala Asp Ala Ala Asn Leu Phe Lys Ala Val Arg Glu Thr Met
            820                 825                 830 gtt gac aca tat gag tct tgt gat gta ctg gct gat ttc tac gac cag      2544
Val Asp Thr Tyr Glu Ser Cys Asp Val Leu Ala Asp Phe Tyr Asp Gln
        835                 840                 845 ttc gct gac cag ttg cac gag tct caa ttg gac aaa atg cca gca ctt      2592
Phe Ala Asp Gln Leu His Glu Ser Gln Leu Asp Lys Met Pro Ala Leu
    850                 855                 860 ccg gct aaa ggt aac ttg aac ctc cgt gac atc tta gag tcg gac ttc      2640
Pro Ala Lys Gly Asn Leu Asn Leu Arg Asp Ile Leu Glu Ser Asp Phe
865                 870                 875                 880 gcg ttc gcg taa                                                       2652
Ala Phe Ala
```

<210> SEQ ID NO 6
<211> LENGTH: 883
<212> TYPE: PRT
<213> ORGANISM: Artificial sequence
<220> FEATURE:
<223> OTHER INFORMATION: Description of the artificial sequence: mutated
      sequences of bacteriophage T7 RNA polymerase

<400> SEQUENCE: 6

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Val Lys Thr Thr Leu Ala Cys Leu Thr Ser
        115                 120                 125
```

-continued

```
Ala Asp Asn Thr Thr Val Gln Ala Val Ala Ser Ala Ile Gly Arg Ala
            130                 135                 140

Ile Glu Asn Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
```

```
                545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
                580                 585                 590

Glu Val Thr Val Thr Asp Glu Asn Thr Gly Glu Ile Ser Glu Lys
                595                 600                 605

Val Lys Leu Gly Thr Lys Ala Leu Ala Gly Gln Trp Leu Ala Tyr Gly
                610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
                675                 680                 685

Val Val Ala Ala Val Glu Ala Met Asn Trp Leu Lys Ser Ala Ala Lys
                690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
                740                 745                 750

Gly Gln Phe Arg Leu Gln Pro Thr Ile Asn Thr Asn Lys Asp Ser Glu
                755                 760                 765

Ile Asp Ala His Lys Gln Glu Ser Gly Ile Ala Pro Asn Phe Val His
                770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
                835                 840                 845

Phe Ala Asp Gln Leu His Glu Ser Gln Leu Asp Lys Met Pro Ala Leu
                850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 7
<211> LENGTH: 2652
<212> TYPE: DNA
<213> ORGANISM: Artificial sequence
<220> FEATURE:
<223> OTHER INFORMATION: Description of the artificial sequence: mutated
      sequences of bacteriophage T7 RNA polymerase
<220> FEATURE:
<221> NAME/KEY: CDS
<222> LOCATION: (1)..(2652)

<400> SEQUENCE: 7 atg aac acg att aac atc gct aag aac gac ttc tct gac atc gaa ctg      48
```

```
                Met Asn Thr Ile Asn Ile Ala Lys Asn Asp Phe Ser Asp Ile Glu Leu
                1               5                   10                  15 gct gct atc ccg ttc aac act ctg gct gac cat tac ggt gag cgt tta              96
Ala Ala Ile Pro Phe Asn Thr Leu Ala Asp His Tyr Gly Glu Arg Leu
                20                  25                  30 gct cgc gaa cag ttg gcc ctt gag cat gag tct tac gag atg ggt gaa             144
Ala Arg Glu Gln Leu Ala Leu Glu His Glu Ser Tyr Glu Met Gly Glu
        35                  40                  45 gca cgc ttc cgc aag atg ttt gag cgt caa ctt aaa gct ggt gag gtt             192
Ala Arg Phe Arg Lys Met Phe Glu Arg Gln Leu Lys Ala Gly Glu Val
    50                  55                  60 gcg gat aac gct gcc gcc aag cct ctc atc act acc cta ctc cct aag             240
Ala Asp Asn Ala Ala Ala Lys Pro Leu Ile Thr Thr Leu Leu Pro Lys
65                  70                  75                  80 atg att gca cgc atc aac gac tgg ttt gag gaa gtg aaa gct aag cgc             288
Met Ile Ala Arg Ile Asn Asp Trp Phe Glu Glu Val Lys Ala Lys Arg
                85                  90                  95 ggc aag cgc ccg aca gcc ttc cag ttc ctg caa gaa atc aag ccg gaa             336
Gly Lys Arg Pro Thr Ala Phe Gln Phe Leu Gln Glu Ile Lys Pro Glu
            100                 105                 110 gcc gta gcg tac atc acc att aag acc act ctg gct tgc cta acc agt             384
Ala Val Ala Tyr Ile Thr Ile Lys Thr Thr Leu Ala Cys Leu Thr Ser
        115                 120                 125 gct gac aat aca acc gtt cag gct gta gca agc gca atc ggt cgg gcc             432
Ala Asp Asn Thr Thr Val Gln Ala Val Ala Ser Ala Ile Gly Arg Ala
    130                 135                 140 att gag gac gag gct cgc ttc ggt cgt atc cgt gac ctt gaa gct aag             480
Ile Glu Asp Glu Ala Arg Phe Gly Arg Ile Arg Asp Leu Glu Ala Lys
145                 150                 155                 160 cac ttc aag aaa aac gtt gag gaa caa ctc aac aag cgc gta ggg cac             528
His Phe Lys Lys Asn Val Glu Glu Gln Leu Asn Lys Arg Val Gly His
                165                 170                 175 gtc tac aag aaa gca ttt atg caa gtt gtc gag gct gac atg ctc tct             576
Val Tyr Lys Lys Ala Phe Met Gln Val Val Glu Ala Asp Met Leu Ser
            180                 185                 190 aag ggt cta ctc ggt ggc gag gcg tgg tct tcg tgg cat aag gaa gac             624
Lys Gly Leu Leu Gly Gly Glu Ala Trp Ser Ser Trp His Lys Glu Asp
        195                 200                 205 tct att cat gta gga gta cgc tgc atc gag atg ctc att gag tca acc             672
Ser Ile His Val Gly Val Arg Cys Ile Glu Met Leu Ile Glu Ser Thr
    210                 215                 220 gga atg gtt agc tta cgc cgc caa aat gct ggc gta gta ggt caa gac             720
Gly Met Val Ser Leu Arg Arg Gln Asn Ala Gly Val Val Gly Gln Asp
225                 230                 235                 240 tct gag act atc gaa ctc gca cct gaa tac gct gag gct atc gca acc             768
Ser Glu Thr Ile Glu Leu Ala Pro Glu Tyr Ala Glu Ala Ile Ala Thr
                245                 250                 255 cgt gca ggt gcg ctg gct ggc atc tct ccg atg ttc caa cct tgc gta             816
Arg Ala Gly Ala Leu Ala Gly Ile Ser Pro Met Phe Gln Pro Cys Val
            260                 265                 270 gtt cct cct aag ccg tgg act ggc att act ggt ggc ggc tat tgg gct             864
Val Pro Pro Lys Pro Trp Thr Gly Ile Thr Gly Gly Gly Tyr Trp Ala
        275                 280                 285 aac ggt tgt cgt cct ctg gcg ctg gtg cgt act cac agt aag aaa gca             912
Asn Gly Cys Arg Pro Leu Ala Leu Val Arg Thr His Ser Lys Lys Ala
    290                 295                 300 ctg atg cgc tac gaa gac gtt tac atg cct gag gtg tac aaa gcg att             960
Leu Met Arg Tyr Glu Asp Val Tyr Met Pro Glu Val Tyr Lys Ala Ile
305                 310                 315                 320
```

```
aac att gcg caa aac acc gca tgg aaa atc aac aag aaa gtc cta gcg      1008
Asn Ile Ala Gln Asn Thr Ala Trp Lys Ile Asn Lys Lys Val Leu Ala
            325                 330                 335 gtc gcc aac gta atc acc aag tgg aag cat tgt ccg gtc gag gac atc      1056
Val Ala Asn Val Ile Thr Lys Trp Lys His Cys Pro Val Glu Asp Ile
    340                 345                 350 cct gcg att gag cgt gaa gaa ctc ccg atg aaa ccg gaa gac atc gac      1104
Pro Ala Ile Glu Arg Glu Glu Leu Pro Met Lys Pro Glu Asp Ile Asp
355                 360                 365 atg aat cct gag gct ctc acc gcg tgg aaa cgt gct gcc gct gct gtg      1152
Met Asn Pro Glu Ala Leu Thr Ala Trp Lys Arg Ala Ala Ala Ala Val
        370                 375                 380 tac cgc aag gac aag gct cgc aag tct cgc cgt atc agc ctt gag ttc      1200
Tyr Arg Lys Asp Lys Ala Arg Lys Ser Arg Arg Ile Ser Leu Glu Phe
385                 390                 395                 400 atg ctt gag caa gcc aat aag ttt gct aac cat aag gcc atc tgg ttc      1248
Met Leu Glu Gln Ala Asn Lys Phe Ala Asn His Lys Ala Ile Trp Phe
            405                 410                 415 cct tac aac atg gac tgg cgc ggt cgt gtt tac gct gtg tca atg ttc      1296
Pro Tyr Asn Met Asp Trp Arg Gly Arg Val Tyr Ala Val Ser Met Phe
        420                 425                 430 aac ccg caa ggt aac gat atg acc aaa gga ctg ctt acg ctg gcg aaa      1344
Asn Pro Gln Gly Asn Asp Met Thr Lys Gly Leu Leu Thr Leu Ala Lys
    435                 440                 445 ggt aaa cca atc ggt aag gaa ggt tac tac tgg ctg aaa atc cac ggt      1392
Gly Lys Pro Ile Gly Lys Glu Gly Tyr Tyr Trp Leu Lys Ile His Gly
450                 455                 460 gca aac tgt gcg ggt gtc gat aag gtt ccg ttc cct gag cgc atc aag      1440
Ala Asn Cys Ala Gly Val Asp Lys Val Pro Phe Pro Glu Arg Ile Lys
465                 470                 475                 480 ttc att gag gaa aac cac gag aac atc atg gct tgc gct aag tct cca      1488
Phe Ile Glu Glu Asn His Glu Asn Ile Met Ala Cys Ala Lys Ser Pro
            485                 490                 495 ctg gag aac act tgg tgg gct gag caa gat tct ccg ttc tgc ttc ctt      1536
Leu Glu Asn Thr Trp Trp Ala Glu Gln Asp Ser Pro Phe Cys Phe Leu
        500                 505                 510 gcg ttc tgc ttt gag tac gct ggg gta cag cac cac ggc ctg agc tat      1584
Ala Phe Cys Phe Glu Tyr Ala Gly Val Gln His His Gly Leu Ser Tyr
    515                 520                 525 aac tgc tcc ctt ccg ctg gcg ttt gac ggg tct tgc tct ggc atc cag      1632
Asn Cys Ser Leu Pro Leu Ala Phe Asp Gly Ser Cys Ser Gly Ile Gln
530                 535                 540 cac ttc tcc gcg atg ctc cga gat gag gta ggt ggt cgc gcg gtt aac      1680
His Phe Ser Ala Met Leu Arg Asp Glu Val Gly Gly Arg Ala Val Asn
545                 550                 555                 560 ttg ctt cct agt gaa acc gtt cag gac atc tac ggg att gtt gct aag      1728
Leu Leu Pro Ser Glu Thr Val Gln Asp Ile Tyr Gly Ile Val Ala Lys
            565                 570                 575 aaa gtc aac gag att cta caa gca gac gca atc aat ggg acc gat aac      1776
Lys Val Asn Glu Ile Leu Gln Ala Asp Ala Ile Asn Gly Thr Asp Asn
        580                 585                 590 gaa gta gtt acc gtg acc gat gag aac act ggt gaa atc tct gag aaa      1824
Glu Val Val Thr Val Thr Asp Glu Asn Thr Gly Glu Ile Ser Glu Lys
    595                 600                 605 gtc aag ctg ggc act aag gca ctg gct ggt caa tgg ctg gct tac ggt      1872
Val Lys Leu Gly Thr Lys Ala Leu Ala Gly Gln Trp Leu Ala Tyr Gly
610                 615                 620 gtt act cgc agt gtg act aag cgt tca gtc atg acg ctg gct tac ggg      1920
Val Thr Arg Ser Val Thr Lys Arg Ser Val Met Thr Leu Ala Tyr Gly
625                 630                 635                 640
```

```
tcc aaa gag ttc ggc ttc cgt caa caa gtg ctg gaa gat acc att cag    1968
Ser Lys Glu Phe Gly Phe Arg Gln Gln Val Leu Glu Asp Thr Ile Gln
            645                 650                 655 cca gct att gat tcc ggc aag ggt ctg atg ttc act cag ccg aat cag    2016
Pro Ala Ile Asp Ser Gly Lys Gly Leu Met Phe Thr Gln Pro Asn Gln
            660                 665                 670 gct gct gga tac atg gct aag ctg att tgg gaa tct gtg agc gtg acg    2064
Ala Ala Gly Tyr Met Ala Lys Leu Ile Trp Glu Ser Val Ser Val Thr
            675                 680                 685 gtg gta gct gcg gtt gaa gca atg aac tgg ctt aag tct gct gct aag    2112
Val Val Ala Ala Val Glu Ala Met Asn Trp Leu Lys Ser Ala Ala Lys
            690                 695                 700 ctg ctg gct gct gag gtc aaa gat aag aag act gga gag att ctt cgc    2160
Leu Leu Ala Ala Glu Val Lys Asp Lys Lys Thr Gly Glu Ile Leu Arg
705                 710                 715                 720 aag cgt tgc gct gtg cat tgg gta act cct gat ggt ttc cct gtg tgg    2208
Lys Arg Cys Ala Val His Trp Val Thr Pro Asp Gly Phe Pro Val Trp
            725                 730                 735 cag gaa tac aag aag cct att cag acg cgc ttg aac ctg atg ttc ctc    2256
Gln Glu Tyr Lys Lys Pro Ile Gln Thr Arg Leu Asn Leu Met Phe Leu
            740                 745                 750 ggt cag ttc cgc tta cag cct acc att aac acc aac aaa gat agc gag    2304
Gly Gln Phe Arg Leu Gln Pro Thr Ile Asn Thr Asn Lys Asp Ser Glu
            755                 760                 765 att gat gca cac aaa cag gag tct ggt atc gct cct aac ttt gta cac    2352
Ile Asp Ala His Lys Gln Glu Ser Gly Ile Ala Pro Asn Phe Val His
            770                 775                 780 agc caa gac ggt agc cac ctt cgt aag act gta gtg tgg gca cac gag    2400
Ser Gln Asp Gly Ser His Leu Arg Lys Thr Val Val Trp Ala His Glu
785                 790                 795                 800 aag tac gga atc gaa tct ttt gca ctg att cac gac tcc ttc ggt acc    2448
Lys Tyr Gly Ile Glu Ser Phe Ala Leu Ile His Asp Ser Phe Gly Thr
            805                 810                 815 att ccg gct gac gct gcg aac ctg ttc aaa gca gtg cgc gaa act atg    2496
Ile Pro Ala Asp Ala Ala Asn Leu Phe Lys Ala Val Arg Glu Thr Met
            820                 825                 830 gtt gac aca tat gag tct tgt gat gta ctg gct gat ttc tac gac cag    2544
Val Asp Thr Tyr Glu Ser Cys Asp Val Leu Ala Asp Phe Tyr Asp Gln
            835                 840                 845 ttc gct gac cag ttg cac gag tct caa ttg gac aaa atg cca gca ctt    2592
Phe Ala Asp Gln Leu His Glu Ser Gln Leu Asp Lys Met Pro Ala Leu
            850                 855                 860 ccg gct aaa ggt aac ttg aac ctc cgt gac atc tta gag tcg gac ttc    2640
Pro Ala Lys Gly Asn Leu Asn Leu Arg Asp Ile Leu Glu Ser Asp Phe
865                 870                 875                 880 gcg ttc gcg taa                                                    2652
Ala Phe Ala <210> SEQ ID NO 8
<211> LENGTH: 883
<212> TYPE: PRT
<213> ORGANISM: Artificial sequence
<220> FEATURE:
<223> OTHER INFORMATION: Description of the artificial sequence: mutated
      sequences of bacteriophage T7 RNA polymerase

<400> SEQUENCE: 8

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
```

-continued

```
                    20                  25                  30
Ala Arg Glu Gln Leu Ala Leu Glu His Glu Ser Tyr Glu Met Gly Glu
             35                  40                  45
Ala Arg Phe Arg Lys Met Phe Glu Arg Gln Leu Lys Ala Gly Glu Val
         50                  55                  60
Ala Asp Asn Ala Ala Ala Lys Pro Leu Ile Thr Thr Leu Leu Pro Lys
 65                  70                  75                  80
Met Ile Ala Arg Ile Asn Asp Trp Phe Glu Val Lys Ala Lys Arg
                 85                  90                  95
Gly Lys Arg Pro Thr Ala Phe Gln Phe Leu Gln Glu Ile Lys Pro Glu
                100                 105                 110
Ala Val Ala Tyr Ile Thr Ile Lys Thr Thr Leu Ala Cys Leu Thr Ser
             115                 120                 125
Ala Asp Asn Thr Thr Val Gln Ala Val Ala Ser Ala Ile Gly Arg Ala
         130                 135                 140
Ile Glu Asp Glu Ala Arg Phe Gly Arg Ile Arg Asp Leu Glu Ala Lys
145                 150                 155                 160
His Phe Lys Lys Asn Val Glu Glu Gln Leu Asn Lys Arg Val Gly His
                165                 170                 175
Val Tyr Lys Lys Ala Phe Met Gln Val Val Glu Ala Asp Met Leu Ser
                180                 185                 190
Lys Gly Leu Leu Gly Gly Glu Ala Trp Ser Ser Trp His Lys Glu Asp
             195                 200                 205
Ser Ile His Val Gly Val Arg Cys Ile Glu Met Leu Ile Glu Ser Thr
         210                 215                 220
Gly Met Val Ser Leu Arg Arg Gln Asn Ala Gly Val Val Gly Gln Asp
225                 230                 235                 240
Ser Glu Thr Ile Glu Leu Ala Pro Glu Tyr Ala Glu Ala Ile Ala Thr
                245                 250                 255
Arg Ala Gly Ala Leu Ala Gly Ile Ser Pro Met Phe Gln Pro Cys Val
             260                 265                 270
Val Pro Pro Lys Pro Trp Thr Gly Ile Thr Gly Gly Gly Tyr Trp Ala
         275                 280                 285
Asn Gly Cys Arg Pro Leu Ala Leu Val Arg Thr His Ser Lys Lys Ala
290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
                325                 330                 335
Val Ala Asn Val Ile Thr Lys Trp Lys His Cys Pro Val Glu Asp Ile
             340                 345                 350
Pro Ala Ile Glu Arg Glu Leu Pro Met Lys Pro Glu Asp Ile Asp
         355                 360                 365
Met Asn Pro Glu Ala Leu Thr Ala Trp Lys Arg Ala Ala Ala Val
     370                 375                 380
Tyr Arg Lys Asp Lys Ala Arg Lys Ser Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
             420                 425                 430
Asn Pro Gln Gly Asn Asp Met Thr Lys Gly Leu Leu Thr Leu Ala Lys
         435                 440                 445
```

-continued

```
Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
850                 855                 860
```

```
Pro Ala Lys Gly Asn Leu Asn Leu Arg Asp Ile Leu Glu Ser Asp Phe
865                 870                 875                 880

Ala Phe Ala

<210> SEQ ID NO 9
<211> LENGTH: 2652
<212> TYPE: DNA
<213> ORGANISM: Artificial sequence
<220> FEATURE:
<223> OTHER INFORMATION: Description of the artificial sequence: mutated
      sequences of bacteriophage T7 RNA polymerase
<220> FEATURE:
<221> NAME/KEY: CDS
<222> LOCATION: (1)..(2652)

<400> SEQUENCE: 9 atg aac acg att aac atc gct aag aac gac ttc tct gac atc gaa ctg      48
Met Asn Thr Ile Asn Ile Ala Lys Asn Asp Phe Ser Asp Ile Glu Leu
1               5                   10                  15 gct gct atc ccg ttc aac act ctg gct gac cat tac ggt gag cgt tta      96
Ala Ala Ile Pro Phe Asn Thr Leu Ala Asp His Tyr Gly Glu Arg Leu
            20                  25                  30 gct cgc gaa cag ttg gcc ctt gag cat gag tct tac gag atg ggt gaa     144
Ala Arg Glu Gln Leu Ala Leu Glu His Glu Ser Tyr Glu Met Gly Glu
        35                  40                  45 gca cgc ttc cgc aag atg ttt gag cgt caa ctt aaa gct ggt gag gtt     192
Ala Arg Phe Arg Lys Met Phe Glu Arg Gln Leu Lys Ala Gly Glu Val
    50                  55                  60 gcg gat aac gct gcc gcc aag cct ctc atc act acc cta ctc cct aag     240
Ala Asp Asn Ala Ala Ala Lys Pro Leu Ile Thr Thr Leu Leu Pro Lys
65                  70                  75                  80 atg att gca cgc atc aac gac tgg ttt gag gaa gtg aaa gct aag cgc     288
Met Ile Ala Arg Ile Asn Asp Trp Phe Glu Glu Val Lys Ala Lys Arg
                85                  90                  95 ggc aag cgc ccg aca gcc ttc cag ttc ctg caa gaa atc aag ccg gaa     336
Gly Lys Arg Pro Thr Ala Phe Gln Phe Leu Gln Glu Ile Lys Pro Glu
            100                 105                 110 gcc gta gcg tac atc acc att aag acc act ctg gct tgc cta acc agt     384
Ala Val Ala Tyr Ile Thr Ile Lys Thr Thr Leu Ala Cys Leu Thr Ser
        115                 120                 125 gct gac aat aca acc gtt cag gct gta gca agc gca atc ggt cgg gcc     432
Ala Asp Asn Thr Thr Val Gln Ala Val Ala Ser Ala Ile Gly Arg Ala
    130                 135                 140 att gag gac gag gct cgc ttc ggt cgt atc cgt gac ctt gaa gct aag     480
Ile Glu Asp Glu Ala Arg Phe Gly Arg Ile Arg Asp Leu Glu Ala Lys
145                 150                 155                 160 cac ttc aag aaa aac gtt gag gaa caa ctc aac aag cgc gta ggg cac     528
His Phe Lys Lys Asn Val Glu Glu Gln Leu Asn Lys Arg Val Gly His
                165                 170                 175 gtc tac aag aaa gca ttt atg caa gtt gtc gag gct gac atg ctc tct     576
Val Tyr Lys Lys Ala Phe Met Gln Val Val Glu Ala Asp Met Leu Ser
            180                 185                 190 aag ggt cta ctc ggt ggc gag gcg tgg tct tcg tgg cat aag gaa gac     624
Lys Gly Leu Leu Gly Gly Glu Ala Trp Ser Ser Trp His Lys Glu Asp
        195                 200                 205 tct att cat gta gga gta cgc tgc atc gag atg ctc att gag tca acc     672
Ser Ile His Val Gly Val Arg Cys Ile Glu Met Leu Ile Glu Ser Thr
    210                 215                 220 gga atg gtt agc tta cac cgc caa aat gct ggc gta gta ggt caa gac     720
Gly Met Val Ser Leu His Arg Gln Asn Ala Gly Val Val Gly Gln Asp
225                 230                 235                 240
```

```
tct gag act atc gaa ctc gca cct gaa tac gct gag gct atc gca acc      768
Ser Glu Thr Ile Glu Leu Ala Pro Glu Tyr Ala Glu Ala Ile Ala Thr
            245                 250                 255 cgt gca ggt gcg ctg gct ggc atc tct ctg atg ttc caa cct tgc gta      816
Arg Ala Gly Ala Leu Ala Gly Ile Ser Leu Met Phe Gln Pro Cys Val
        260                 265                 270 gtt cct cct aag ccg tgg act ggc att act ggt ggt ggc tat tgg gct      864
Val Pro Pro Lys Pro Trp Thr Gly Ile Thr Gly Gly Gly Tyr Trp Ala
    275                 280                 285 aac ggt cgt cgt cct ctg gcg ctg gtg cgt act cac agt aag aaa gca      912
Asn Gly Arg Arg Pro Leu Ala Leu Val Arg Thr His Ser Lys Lys Ala
290                 295                 300 ctg atg cgc tac gaa gac gtt tac atg cct gag gtg tac aaa gcg att      960
Leu Met Arg Tyr Glu Asp Val Tyr Met Pro Glu Val Tyr Lys Ala Ile
305                 310                 315                 320 aac att gcg caa aac acc gca tgg aaa atc aac aag aaa gtc cta gcg     1008
Asn Ile Ala Gln Asn Thr Ala Trp Lys Ile Asn Lys Lys Val Leu Ala
                325                 330                 335 gtc gcc aac gta atc acc aag tgg aag cat tgt ccg gtc gag gac atc     1056
Val Ala Asn Val Ile Thr Lys Trp Lys His Cys Pro Val Glu Asp Ile
            340                 345                 350 cct gcg att gag cgt gaa gaa ctc ccg atg aaa ccg gaa gac atc gac     1104
Pro Ala Ile Glu Arg Glu Glu Leu Pro Met Lys Pro Glu Asp Ile Asp
        355                 360                 365 atg aat cct gag gct ctc acc gcg tgg aaa cgt gct gcc gct gct gtg     1152
Met Asn Pro Glu Ala Leu Thr Ala Trp Lys Arg Ala Ala Ala Ala Val
    370                 375                 380 tac cgc aag gac aag gct cgc aag tct cgc cgt atc agc ctt gag ttc     1200
Tyr Arg Lys Asp Lys Ala Arg Lys Ser Arg Arg Ile Ser Leu Glu Phe
385                 390                 395                 400 atg ctt gag caa gcc aat aag ttt gct aac cat aag gcc atc tgg ttc     1248
Met Leu Glu Gln Ala Asn Lys Phe Ala Asn His Lys Ala Ile Trp Phe
                405                 410                 415 cct tac aac atg gac tgg cgc ggt cgt gtt tac gct gtg tca atg ttc     1296
Pro Tyr Asn Met Asp Trp Arg Gly Arg Val Tyr Ala Val Ser Met Phe
            420                 425                 430 aac ccg caa ggt aac gat atg acc aaa gga ctg ctt acg ctg gcg aaa     1344
Asn Pro Gln Gly Asn Asp Met Thr Lys Gly Leu Leu Thr Leu Ala Lys
        435                 440                 445 ggt aaa cca atc ggt aag gaa ggt tac tac tgg ctg aaa atc cac ggt     1392
Gly Lys Pro Ile Gly Lys Glu Gly Tyr Tyr Trp Leu Lys Ile His Gly
    450                 455                 460 gca aac tgt gcg ggt gtc gat aag gtt ccg ttc cct gag cgc atc aag     1440
Ala Asn Cys Ala Gly Val Asp Lys Val Pro Phe Pro Glu Arg Ile Lys
465                 470                 475                 480 ttc att gag gaa aac cac gag aac atc atg gct tgc gct aag tct cca     1488
Phe Ile Glu Glu Asn His Glu Asn Ile Met Ala Cys Ala Lys Ser Pro
                485                 490                 495 ctg gag aac act tgg tgg gct gag caa gat tct ccg ttc tgc ttc ctt     1536
Leu Glu Asn Thr Trp Trp Ala Glu Gln Asp Ser Pro Phe Cys Phe Leu
            500                 505                 510 gcg ttc tgc ttt gag tac gct ggg gta cag cac cac ggc ctg agc tat     1584
Ala Phe Cys Phe Glu Tyr Ala Gly Val Gln His His Gly Leu Ser Tyr
        515                 520                 525 aac tgc tcc ctt ccg ctg gcg ttt gac ggg tct tgc tct ggc atc cag     1632
Asn Cys Ser Leu Pro Leu Ala Phe Asp Gly Ser Cys Ser Gly Ile Gln
    530                 535                 540 cac ttc tcc gcg atg ctc cga gat gag gta ggt ggt cgc gcg gtt aac     1680
His Phe Ser Ala Met Leu Arg Asp Glu Val Gly Gly Arg Ala Val Asn
545                 550                 555                 560
```

| | | |
|---|---|---|
| ttg ctt cct agt gaa acc gtt cag gac atc tac ggg att gtt gct aag<br>Leu Leu Pro Ser Glu Thr Val Gln Asp Ile Tyr Gly Ile Val Ala Lys<br>565                            570                           575 | 1728 |
| aaa gtc aac gag att cta caa gca gac gca atc aat ggg acc gat aac<br>Lys Val Asn Glu Ile Leu Gln Ala Asp Ala Ile Asn Gly Thr Asp Asn<br>      580                          585                           590 | 1776 |
| gaa gta gtt acc gtg acc gat gag aac act ggt gaa atc tct gag aaa<br>Glu Val Val Thr Val Thr Asp Glu Asn Thr Gly Glu Ile Ser Glu Lys<br>           595                          600                        605 | 1824 |
| gtc aag ctg ggc act aag gca ctg gct ggt caa tgg ctg gct tac ggt<br>Val Lys Leu Gly Thr Lys Ala Leu Ala Gly Gln Trp Leu Ala Tyr Gly<br>610                            615                           620 | 1872 |
| gtt act cgc agt gtg act aag cgt tca gtc atg acg ctg gct ttc ggg<br>Val Thr Arg Ser Val Thr Lys Arg Ser Val Met Thr Leu Ala Phe Gly<br>625                            630                           635                        640 | 1920 |
| tcc aaa gag ttc ggc ttc cgt caa caa gtg ctg gaa gat acc att cag<br>Ser Lys Glu Phe Gly Phe Arg Gln Gln Val Leu Glu Asp Thr Ile Gln<br>                645                           650                        655 | 1968 |
| cca gct att gat tcc ggc aag ggt ctg atg ttc act cag ccg aat cag<br>Pro Ala Ile Asp Ser Gly Lys Gly Leu Met Phe Thr Gln Pro Asn Gln<br>                       660                           665                        670 | 2016 |
| gct gct gga tac atg gct aag ctg att tgg gaa tct gtg agc gtg acg<br>Ala Ala Gly Tyr Met Ala Lys Leu Ile Trp Glu Ser Val Ser Val Thr<br>675                            680                           685 | 2064 |
| gtg gta gct gcg gtt gaa gca atg aac tgg ctt aag tct gct gct aag<br>Val Val Ala Ala Val Glu Ala Met Asn Trp Leu Lys Ser Ala Ala Lys<br>      690                          695                           700 | 2112 |
| ctg ctg gct gct gag gtc aaa gat aag aag act gga gag att ctt cgc<br>Leu Leu Ala Ala Glu Val Lys Asp Lys Lys Thr Gly Glu Ile Leu Arg<br>705                            710                           715                        720 | 2160 |
| aag cgt tgc gct gtg cat tgg gta act cct gat ggt ttc cct gtg tgg<br>Lys Arg Cys Ala Val His Trp Val Thr Pro Asp Gly Phe Pro Val Trp<br>                     725                           730                        735 | 2208 |
| cag gaa tac aag aag cct att cag acg cgc ttg aac ctg atg ttc ctc<br>Gln Glu Tyr Lys Lys Pro Ile Gln Thr Arg Leu Asn Leu Met Phe Leu<br>                740                           745                        750 | 2256 |
| ggt cag ttc cgc tta cag cct acc att aac acc aac aaa gat agc gag<br>Gly Gln Phe Arg Leu Gln Pro Thr Ile Asn Thr Asn Lys Asp Ser Glu<br>           755                          760                        765 | 2304 |
| att gat gca cac aaa cag gag tct ggt atc gct cct aac ttt gta cac<br>Ile Asp Ala His Lys Gln Glu Ser Gly Ile Ala Pro Asn Phe Val His<br>770                            775                           780 | 2352 |
| agc caa gac ggt agc cac ctt cgt aag act gta gtg tgg gca cac gag<br>Ser Gln Asp Gly Ser His Leu Arg Lys Thr Val Val Trp Ala His Glu<br>785                            790                           795                        800 | 2400 |
| aag tac gga atc gaa tct ttt gca ctg att cac gac tcc ttc ggt acc<br>Lys Tyr Gly Ile Glu Ser Phe Ala Leu Ile His Asp Ser Phe Gly Thr<br>                     805                           810                        815 | 2448 |
| att ccg gct gac gct gcg aac ctg ttc aaa gca gtg cgc gaa act atg<br>Ile Pro Ala Asp Ala Ala Asn Leu Phe Lys Ala Val Arg Glu Thr Met<br>          820                          825                           830 | 2496 |
| gtt gac aca tat gag tct tgt gat gta ctg gct gat ttc tac gac cag<br>Val Asp Thr Tyr Glu Ser Cys Asp Val Leu Ala Asp Phe Tyr Asp Gln<br>835                            840                           845 | 2544 |
| ttc gct gac cag ttg cac gag tct caa ttg gac aaa atg cca gca ctt<br>Phe Ala Asp Gln Leu His Glu Ser Gln Leu Asp Lys Met Pro Ala Leu<br>850                            855                           860 | 2592 |
| ccg gct aaa ggt aac ttg aac ctc cgt gac atc tta gag tcg gac ttc<br>Pro Ala Lys Gly Asn Leu Asn Leu Arg Asp Ile Leu Glu Ser Asp Phe | 2640 |

```
                            865                 870                 875                 880 gcg ttc gcg taa                                                                              2652
Ala Phe Ala <210> SEQ ID NO 10
<211> LENGTH: 883
<212> TYPE: PRT
<213> ORGANISM: Artificial sequence
<220> FEATURE:
<223> OTHER INFORMATION: Description of the artificial sequence: mutated
      sequences of bacteriophage T7 RNA polymerase

<400> SEQUENCE: 10

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Leu Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335
```

-continued

```
Val Ala Asn Val Ile Thr Lys Trp Lys His Cys Pro Val Glu Asp Ile
            340                 345                 350
Pro Ala Ile Glu Arg Glu Glu Leu Pro Met Lys Pro Glu Asp Ile Asp
            355                 360                 365
Met Asn Pro Glu Ala Leu Thr Ala Trp Lys Arg Ala Ala Ala Ala Val
370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
            405                 410                 415
Pro Tyr Asn Met Asp Trp Arg Gly Arg Val Tyr Ala Val Ser Met Phe
            420                 425                 430
Asn Pro Gln Gly Asn Asp Met Thr Lys Gly Leu Leu Thr Leu Ala Lys
            435                 440                 445
Gly Lys Pro Ile Gly Lys Glu Gly Tyr Tyr Trp Leu Lys Ile His Gly
450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
            485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
            515                 520                 525
Asn Cys Ser Leu Pro Leu Ala Phe Asp Gly Ser Cys Ser Gly Ile Gln
            530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
            565                 570                 575
Lys Val Asn Glu Ile Leu Gln Ala Asp Ala Ile Asn Gly Thr Asp Asn
            580                 585                 590
Glu Val Val Thr Val Thr Asp Glu Asn Thr Gly Glu Ile Ser Glu Lys
            595                 600                 605
Val Lys Leu Gly Thr Lys Ala Leu Ala Gly Gln Trp Leu Ala Tyr Gly
            610                 615                 620
Val Thr Arg Ser Val Thr Lys Arg Ser Val Met Thr Leu Ala Phe Gly
625                 630                 635                 640
Ser Lys Glu Phe Gly Phe Arg Gln Gln Val Leu Glu Asp Thr Ile Gln
            645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Val Ser Val Thr
            675                 680                 685
Val Val Ala Ala Val Glu Ala Met Asn Trp Leu Lys Ser Ala Ala Lys
            690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
            725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
```

-continued

```
                   755                 760                 765
Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 11
<211> LENGTH: 2652
<212> TYPE: DNA
<213> ORGANISM: Artificial sequence
<220> FEATURE:
<223> OTHER INFORMATION: Description of the artificial sequence: mutated
      sequences of bacteriophage T7 RNA polymerase
<220> FEATURE:
<221> NAME/KEY: CDS
<222> LOCATION: (1)..(2652)

<400> SEQUENCE: 11 atg aac acg att aac atc gct aag aac gac ttc tct gac atc gaa ctg      48
Met Asn Thr Ile Asn Ile Ala Lys Asn Asp Phe Ser Asp Ile Glu Leu
1               5                   10                  15 gct gct atc ccg ttc aac act ctg gct gac cat tac ggt gag cgt tta      96
Ala Ala Ile Pro Phe Asn Thr Leu Ala Asp His Tyr Gly Glu Arg Leu
            20                  25                  30 gct cgc gaa cag ttg gcc ctt gag cat gag tct tac gag atg ggt gaa     144
Ala Arg Glu Gln Leu Ala Leu Glu His Glu Ser Tyr Glu Met Gly Glu
        35                  40                  45 gca cgc ttc cgc aag atg ttt gag cgt caa ctt aaa gct ggt gag gtt     192
Ala Arg Phe Arg Lys Met Phe Glu Arg Gln Leu Lys Ala Gly Glu Val
    50                  55                  60 gcg gat aac gct gcc gcc aag cct ctc atc act acc cta ctc cct aag     240
Ala Asp Asn Ala Ala Ala Lys Pro Leu Ile Thr Thr Leu Leu Pro Lys
65                  70                  75                  80 atg att gca cgc atc aac gac tgg ttt gag gaa gtg aaa gct aag cgc     288
Met Ile Ala Arg Ile Asn Asp Trp Phe Glu Glu Val Lys Ala Lys Arg
                85                  90                  95 ggc aag cgc ccg aca gcc ttc cag ttc ctg caa gaa atc aag ccg gaa     336
Gly Lys Arg Pro Thr Ala Phe Gln Phe Leu Gln Glu Ile Lys Pro Glu
            100                 105                 110 gcc gta gcg tac atc acc att aag acc act ctg gct tgc cta acc agt     384
Ala Val Ala Tyr Ile Thr Ile Lys Thr Thr Leu Ala Cys Leu Thr Ser
        115                 120                 125 gct gac aat aca acc gtt cag gct gta gca agc gca atc ggt cgg gcc     432
Ala Asp Asn Thr Thr Val Gln Ala Val Ala Ser Ala Ile Gly Arg Ala
    130                 135                 140 att gag gac gag gct cgc ttc ggt cgt atc cgt gac ctt gaa gct aag     480
Ile Glu Asp Glu Ala Arg Phe Gly Arg Ile Arg Asp Leu Glu Ala Lys
145                 150                 155                 160
```

```
cac ttc aag aaa aac gtt gag gaa caa ctc aac aag cgc gta ggg cac      528
His Phe Lys Lys Asn Val Glu Glu Gln Leu Asn Lys Arg Val Gly His
            165                 170                 175 gtc tac aag aaa gca ttt atg caa gtt gtc gag gct gac atg ctc tct      576
Val Tyr Lys Lys Ala Phe Met Gln Val Val Glu Ala Asp Met Leu Ser
        180                 185                 190 aag ggt cta ctc ggt ggc gag gcg tgg tct tcg tgg cat aag gaa gac      624
Lys Gly Leu Leu Gly Gly Glu Ala Trp Ser Ser Trp His Lys Glu Asp
    195                 200                 205 tct att cat gta gga gta cgc tgc atc gag atg ctc att gag tca acc      672
Ser Ile His Val Gly Val Arg Cys Ile Glu Met Leu Ile Glu Ser Thr
210                 215                 220 gga atg gtt agc tta cac cgc caa aat gct ggc gta gta ggt caa gac      720
Gly Met Val Ser Leu His Arg Gln Asn Ala Gly Val Val Gly Gln Asp
225                 230                 235                 240 tct gag act atc gaa ctc gca cct gaa tac gct gag gct atc gca acc      768
Ser Glu Thr Ile Glu Leu Ala Pro Glu Tyr Ala Glu Ala Ile Ala Thr
                245                 250                 255 cgt gca ggt gcg ctg gct ggc atc tct ccg atg ttc caa cct tgc gta      816
Arg Ala Gly Ala Leu Ala Gly Ile Ser Pro Met Phe Gln Pro Cys Val
            260                 265                 270 gtt cct cct aag ccg tgg act ggc att act ggt ggt ggc tat tgg gct      864
Val Pro Pro Lys Pro Trp Thr Gly Ile Thr Gly Gly Gly Tyr Trp Ala
        275                 280                 285 aac ggt cgt cgt cct ctg gcg ctg gtg cgt act cac agt aag aaa gca      912
Asn Gly Arg Arg Pro Leu Ala Leu Val Arg Thr His Ser Lys Lys Ala
    290                 295                 300 ctg atg cgc tac gaa gac gtt tac atg cct gag gtg tac aaa gcg att      960
Leu Met Arg Tyr Glu Asp Val Tyr Met Pro Glu Val Tyr Lys Ala Ile
305                 310                 315                 320 aac att gcg caa aac acc gca tgg aaa atc aac aag aaa gtc cta gcg     1008
Asn Ile Ala Gln Asn Thr Ala Trp Lys Ile Asn Lys Lys Val Leu Ala
                325                 330                 335 gtc gcc aac gta atc acc aag tgg aag cat tgt ccg gtc gag gac atc     1056
Val Ala Asn Val Ile Thr Lys Trp Lys His Cys Pro Val Glu Asp Ile
            340                 345                 350 cct gcg att gag cgt gaa gaa ctc ccg atg aaa ccg gaa gac atc gac     1104
Pro Ala Ile Glu Arg Glu Glu Leu Pro Met Lys Pro Glu Asp Ile Asp
        355                 360                 365 atg aat cct gag gct ctc acc gcg tgg aaa cgt gct gcc gct gct gtg     1152
Met Asn Pro Glu Ala Leu Thr Ala Trp Lys Arg Ala Ala Ala Ala Val
    370                 375                 380 tac cgc aag gac aag gct cgc aag tct cgc cgt atc agc ctt gag ttc     1200
Tyr Arg Lys Asp Lys Ala Arg Lys Ser Arg Arg Ile Ser Leu Glu Phe
385                 390                 395                 400 atg ctt gag caa gcc aat aag ttt gct aac cat aag gcc atc tgg ttc     1248
Met Leu Glu Gln Ala Asn Lys Phe Ala Asn His Lys Ala Ile Trp Phe
                405                 410                 415 cct tac aac atg gac tgg cgc ggt cgt gtt tac gct gtg tca atg ttc     1296
Pro Tyr Asn Met Asp Trp Arg Gly Arg Val Tyr Ala Val Ser Met Phe
            420                 425                 430 aac ccg caa ggt aac gat atg acc aaa gga ctg ctt acg ctg gcg aaa     1344
Asn Pro Gln Gly Asn Asp Met Thr Lys Gly Leu Leu Thr Leu Ala Lys
        435                 440                 445 ggt aaa cca atc ggt aag gaa ggt tac tac tgg ctg aaa atc cac ggt     1392
Gly Lys Pro Ile Gly Lys Glu Gly Tyr Tyr Trp Leu Lys Ile His Gly
    450                 455                 460 gca aac tgt gcg ggt gtc gat aag gtt ccg ttc cct gag cgc atc aag     1440
Ala Asn Cys Ala Gly Val Asp Lys Val Pro Phe Pro Glu Arg Ile Lys
465                 470                 475                 480
```

```
                                                                -continued ttc att gag gaa aac cac gag aac atc atg gct tgc gct aag tct cca      1488
Phe Ile Glu Glu Asn His Glu Asn Ile Met Ala Cys Ala Lys Ser Pro
            485                 490                 495 ctg gag aac act tgg tgg gct gag caa gat tct ccg ttc tgc ttc ctt      1536
Leu Glu Asn Thr Trp Trp Ala Glu Gln Asp Ser Pro Phe Cys Phe Leu
        500                 505                 510 gcg ttc tgc ttt gag tac gct ggg gta cag cac cac ggc ctg agc tat      1584
Ala Phe Cys Phe Glu Tyr Ala Gly Val Gln His His Gly Leu Ser Tyr
    515                 520                 525 aac tgc tcc ctt ccg ctg gcg ttt gac ggg tct tgc tct ggc atc cag      1632
Asn Cys Ser Leu Pro Leu Ala Phe Asp Gly Ser Cys Ser Gly Ile Gln
530                 535                 540 cac ttc tcc gcg atg ctc cga gat gag gta ggt ggt cgc gcg gtt aac      1680
His Phe Ser Ala Met Leu Arg Asp Glu Val Gly Gly Arg Ala Val Asn
545                 550                 555                 560 ttg ctt cct agt gaa acc gtt cag gac atc tac ggg att gtt gct aag      1728
Leu Leu Pro Ser Glu Thr Val Gln Asp Ile Tyr Gly Ile Val Ala Lys
            565                 570                 575 aaa gtc aac gag att cta caa gca gac gca atc aat ggg acc gat aac      1776
Lys Val Asn Glu Ile Leu Gln Ala Asp Ala Ile Asn Gly Thr Asp Asn
        580                 585                 590 gaa gta gtt acc gtg acc gat gag aac act ggt gaa atc tct gag aaa      1824
Glu Val Val Thr Val Thr Asp Glu Asn Thr Gly Glu Ile Ser Glu Lys
    595                 600                 605 gtc aag ctg ggc act aag gca ctg gct ggt caa tgg ctg gct tac ggt      1872
Val Lys Leu Gly Thr Lys Ala Leu Ala Gly Gln Trp Leu Ala Tyr Gly
610                 615                 620 gtt act cgc agt gtg act aag cgt tca gtc atg acg ctg gct tac ggg      1920
Val Thr Arg Ser Val Thr Lys Arg Ser Val Met Thr Leu Ala Tyr Gly
625                 630                 635                 640 tcc aaa gag ttc ggc ttc cgt caa caa gtg ctg gaa gat acc att cag      1968
Ser Lys Glu Phe Gly Phe Arg Gln Gln Val Leu Glu Asp Thr Ile Gln
            645                 650                 655 cca gct att gat tcc ggc aag ggt ctg atg ttc act cag ccg aat cag      2016
Pro Ala Ile Asp Ser Gly Lys Gly Leu Met Phe Thr Gln Pro Asn Gln
        660                 665                 670 gct gct gga tac atg gct aag ctg att tgg gaa tct gtg agc gtg acg      2064
Ala Ala Gly Tyr Met Ala Lys Leu Ile Trp Glu Ser Val Ser Val Thr
    675                 680                 685 gtg gta gct gcg gtt gaa gca atg aac tgg ctt aag tct gct gct aag      2112
Val Val Ala Ala Val Glu Ala Met Asn Trp Leu Lys Ser Ala Ala Lys
690                 695                 700 ctg ctg gct gct gag gtc aaa gat aag aag act gga gag att ctt cgc      2160
Leu Leu Ala Ala Glu Val Lys Asp Lys Lys Thr Gly Glu Ile Leu Arg
705                 710                 715                 720 aag cgt tgc gct gtg cat tgg gta act cct gat ggt ttc cct gtg tgg      2208
Lys Arg Cys Ala Val His Trp Val Thr Pro Asp Gly Phe Pro Val Trp
            725                 730                 735 cag gaa tac aag aag cct att cag acg cgc ttg aac ctg atg ttc ctc      2256
Gln Glu Tyr Lys Lys Pro Ile Gln Thr Arg Leu Asn Leu Met Phe Leu
        740                 745                 750 ggt cag ttc cgc tta cag cct acc att aac acc aac aaa gat agc gag      2304
Gly Gln Phe Arg Leu Gln Pro Thr Ile Asn Thr Asn Lys Asp Ser Glu
    755                 760                 765 att gat gca cac aaa cag gag tct ggt atc gct cct aac ttt gta cac      2352
Ile Asp Ala His Lys Gln Glu Ser Gly Ile Ala Pro Asn Phe Val His
770                 775                 780 agc caa gac ggt agc cac ctt cgt aag act gta gtg tgg gca cac gag      2400
Ser Gln Asp Gly Ser His Leu Arg Lys Thr Val Val Trp Ala His Glu
```

-continued

```
                785                 790                 795                 800
aag tac gga atc gaa tct ttt gca ctg aat cac gac tcc ttc ggt acc              2448
Lys Tyr Gly Ile Glu Ser Phe Ala Leu Asn His Asp Ser Phe Gly Thr
                        805                 810                 815 att ccg gct gac gct gcg aac ctg ttc aaa gca gtg cgc gaa act atg              2496
Ile Pro Ala Asp Ala Ala Asn Leu Phe Lys Ala Val Arg Glu Thr Met
                820                 825                 830 gtt gac aca tat gag tct tgt gat gta ctg gct gat ttc tac gac cag              2544
Val Asp Thr Tyr Glu Ser Cys Asp Val Leu Ala Asp Phe Tyr Asp Gln
            835                 840                 845 ttc gct gac cag ttg cac gag tct caa ttg gac aaa atg cca gca ctt              2592
Phe Ala Asp Gln Leu His Glu Ser Gln Leu Asp Lys Met Pro Ala Leu
850                 855                 860 ccg gct aaa ggt aac ttg aac ctc cgt gac atc tta gag tcg gac ttc              2640
Pro Ala Lys Gly Asn Leu Asn Leu Arg Asp Ile Leu Glu Ser Asp Phe
865                 870                 875                 880 gcg ttc gcg taa                                                              2652
Ala Phe Ala <210> SEQ ID NO 12
<211> LENGTH: 883
<212> TYPE: PRT
<213> ORGANISM: Artificial sequence
<220> FEATURE:
<223> OTHER INFORMATION: Description of the artificial sequence: mutated
      sequences of bacteriophage T7 RNA polymerase

<400> SEQUENCE: 12

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
```

-continued

```
            225                 230                 235                 240
Ser Glu Thr Ile Glu Leu Ala Pro Glu Tyr Ala Glu Ile Ala Thr
                245                 250                 255
Arg Ala Gly Ala Leu Ala Gly Ile Ser Pro Met Phe Gln Pro Cys Val
            260                 265                 270
Val Pro Pro Lys Pro Trp Thr Gly Ile Thr Gly Gly Tyr Trp Ala
        275                 280                 285
Asn Gly Arg Arg Pro Leu Ala Leu Val Arg Thr His Ser Lys Lys Ala
        290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
                325                 330                 335
Val Ala Asn Val Ile Thr Lys Trp Lys His Cys Pro Val Glu Asp Ile
            340                 345                 350
Pro Ala Ile Glu Arg Glu Leu Pro Met Lys Pro Glu Asp Ile Asp
        355                 360                 365
Met Asn Pro Glu Ala Leu Thr Ala Trp Lys Arg Ala Ala Ala Val
    370                 375                 380
Tyr Arg Lys Asp Lys Ala Arg Lys Ser Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
            420                 425                 430
Asn Pro Gln Gly Asn Asp Met Thr Lys Gly Leu Leu Thr Leu Ala Lys
        435                 440                 445
Gly Lys Pro Ile Gly Lys Glu Gly Tyr Tyr Trp Leu Lys Ile His Gly
    450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
        515                 520                 525
Asn Cys Ser Leu Pro Leu Ala Phe Asp Gly Ser Cys Ser Gly Ile Gln
        530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
            580                 585                 590
Glu Val Val Thr Val Thr Asp Glu Asn Thr Gly Glu Ile Ser Glu Lys
        595                 600                 605
Val Lys Leu Gly Thr Lys Ala Leu Ala Gly Gln Trp Leu Ala Tyr Gly
    610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                645                 650                 655
```

-continued

```
Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Asn His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 13
<211> LENGTH: 2652
<212> TYPE: DNA
<213> ORGANISM: Artificial sequence
<220> FEATURE:
<223> OTHER INFORMATION: Description of the artificial sequence: mutated
      sequences of bacteriophage T7 RNA polymerase
<220> FEATURE:
<221> NAME/KEY: CDS
<222> LOCATION: (1)..(2652)

<400> SEQUENCE: 13 atg aac acg att aac atc gct aag aac gac ttc tct gac atc gaa ctg      48
Met Asn Thr Ile Asn Ile Ala Lys Asn Asp Phe Ser Asp Ile Glu Leu
1               5                   10                  15 gct gct atc ccg ttc aac act ctg gct gac cat tac ggt gag cgt tta      96
Ala Ala Ile Pro Phe Asn Thr Leu Ala Asp His Tyr Gly Glu Arg Leu
                20                  25                  30 gct cgc gaa cag ttg gcc ctt gag cat gag tct tac gag atg ggt gaa     144
Ala Arg Glu Gln Leu Ala Leu Glu His Glu Ser Tyr Glu Met Gly Glu
            35                  40                  45 gca cgc ttc cgc aag atg ttt gag cgt caa ctt aaa gct ggt gag gtt     192
Ala Arg Phe Arg Lys Met Phe Glu Arg Gln Leu Lys Ala Gly Glu Val
        50                  55                  60 gcg gat aac gct gcc gcc aag cct ctc atc act acc cta ctc cct aag     240
Ala Asp Asn Ala Ala Ala Lys Pro Leu Ile Thr Thr Leu Leu Pro Lys
65                  70                  75                  80
```

-continued

```
atg att gca cgc atc aac gac tgg ttt gag gaa gtg aaa gct aag cgc      288
Met Ile Ala Arg Ile Asn Asp Trp Phe Glu Glu Val Lys Ala Lys Arg
            85                  90                  95 ggc aag cgc ccg aca gcc ttc cag ttc ctg caa gaa atc aag ccg gaa      336
Gly Lys Arg Pro Thr Ala Phe Gln Phe Leu Gln Glu Ile Lys Pro Glu
       100                 105                 110 gcc gta gcg tac atc acc att aag acc act ctg gct tgc cta acc agt      384
Ala Val Ala Tyr Ile Thr Ile Lys Thr Thr Leu Ala Cys Leu Thr Ser
   115                 120                 125 gct gac aat aca acc gtt cag gct gta gca agc gca atc ggt cgg gcc      432
Ala Asp Asn Thr Thr Val Gln Ala Val Ala Ser Ala Ile Gly Arg Ala
130                 135                 140 att gag gac gag gct cgc ttc ggt cgt atc cgt gac ctt gaa gct aag      480
Ile Glu Asp Glu Ala Arg Phe Gly Arg Ile Arg Asp Leu Glu Ala Lys
145                 150                 155                 160 cac ttc aag aaa aac gtt gag gaa caa ctc aac aag cgc gta ggg cac      528
His Phe Lys Lys Asn Val Glu Glu Gln Leu Asn Lys Arg Val Gly His
                165                 170                 175 gtc tac aag aaa gca ttt atg caa gtt gtc gag gct gac atg ctc tct      576
Val Tyr Lys Lys Ala Phe Met Gln Val Val Glu Ala Asp Met Leu Ser
            180                 185                 190 aag ggt cta ctc ggt ggc gag gcg tgg tct tcg tgg cat aag gaa gac      624
Lys Gly Leu Leu Gly Gly Glu Ala Trp Ser Ser Trp His Lys Glu Asp
        195                 200                 205 tct att cat gta gga gta cgc tgc atc gag atg ctc att gag tca acc      672
Ser Ile His Val Gly Val Arg Cys Ile Glu Met Leu Ile Glu Ser Thr
    210                 215                 220 gga atg gtt agc tta cac cgc caa aat gct ggc gta gta ggt caa gac      720
Gly Met Val Ser Leu His Arg Gln Asn Ala Gly Val Val Gly Gln Asp
225                 230                 235                 240 tct gag act atc gaa ctc gca cct gaa tac gct gag gct atc gca acc      768
Ser Glu Thr Ile Glu Leu Ala Pro Glu Tyr Ala Glu Ala Ile Ala Thr
                245                 250                 255 cgt gca ggt gcg ctg gct ggc atc tct ctg atg ttc caa cct tgc gta      816
Arg Ala Gly Ala Leu Ala Gly Ile Ser Leu Met Phe Gln Pro Cys Val
            260                 265                 270 gtt cct cct aag ccg tgg act ggc att act ggt ggc ggc tat tgg gct      864
Val Pro Pro Lys Pro Trp Thr Gly Ile Thr Gly Gly Gly Tyr Trp Ala
        275                 280                 285 aac ggt cgt cgt cct ctg gcg ctg gtg cgt act cac agt aag aaa gca      912
Asn Gly Arg Arg Pro Leu Ala Leu Val Arg Thr His Ser Lys Lys Ala
    290                 295                 300 ctg atg cgc tac gaa gac gtt tac atg cct gag gtg tac aaa gcg att      960
Leu Met Arg Tyr Glu Asp Val Tyr Met Pro Glu Val Tyr Lys Ala Ile
305                 310                 315                 320 aac att gcg caa aac acc gca tgg aaa atc aac aag aaa gtc cta gcg     1008
Asn Ile Ala Gln Asn Thr Ala Trp Lys Ile Asn Lys Lys Val Leu Ala
                325                 330                 335 gtc gcc aac gta atc acc aag tgg aag cat tgt ccg gtc gag gac atc     1056
Val Ala Asn Val Ile Thr Lys Trp Lys His Cys Pro Val Glu Asp Ile
            340                 345                 350 cct gcg att gag cgt gaa gaa ctc ccg atg aaa ccg gaa gac atc gac     1104
Pro Ala Ile Glu Arg Glu Glu Leu Pro Met Lys Pro Glu Asp Ile Asp
        355                 360                 365 atg aat cct gag gct ctc acc gcg tgg aaa cgt gct gcc gct gct gtg     1152
Met Asn Pro Glu Ala Leu Thr Ala Trp Lys Arg Ala Ala Ala Ala Val
    370                 375                 380 tac cgc aag gac aag gct cgc aag tct cgc cgt atc agc ctt gag ttc     1200
Tyr Arg Lys Asp Lys Ala Arg Lys Ser Arg Arg Ile Ser Leu Glu Phe
385                 390                 395                 400
```

```
atg ctt gag caa gcc aat aag ttt gct aac cat aag gcc atc tgg ttc     1248
Met Leu Glu Gln Ala Asn Lys Phe Ala Asn His Lys Ala Ile Trp Phe
            405                 410                 415 cct tac aac atg gac tgg cgc ggt cgt gtt tac gct gtg tca atg ttc     1296
Pro Tyr Asn Met Asp Trp Arg Gly Arg Val Tyr Ala Val Ser Met Phe
        420                 425                 430 aac ccg caa ggt aac gat atg acc aaa gga ctg ctt acg ctg gcg aaa     1344
Asn Pro Gln Gly Asn Asp Met Thr Lys Gly Leu Leu Thr Leu Ala Lys
    435                 440                 445 ggt aaa cca atc ggt aag gaa ggt tac tac tgg ctg aaa atc cac ggt     1392
Gly Lys Pro Ile Gly Lys Glu Gly Tyr Tyr Trp Leu Lys Ile His Gly
450                 455                 460 gca aac tgt gcg ggt gtc gat aag gtt ccg ttc cct gag cgc atc aag     1440
Ala Asn Cys Ala Gly Val Asp Lys Val Pro Phe Pro Glu Arg Ile Lys
465                 470                 475                 480 ttc att gag gaa aac cac gag aac atc atg gct tgc gct aag tct cca     1488
Phe Ile Glu Glu Asn His Glu Asn Ile Met Ala Cys Ala Lys Ser Pro
                485                 490                 495 ctg gag aac act tgg tgg gct gag caa gat tct ccg ttc tgc ttc ctt     1536
Leu Glu Asn Thr Trp Trp Ala Glu Gln Asp Ser Pro Phe Cys Phe Leu
            500                 505                 510 gcg ttc tgc ttt gag tac gct ggg gta cag cac cac ggc ctg agc tat     1584
Ala Phe Cys Phe Glu Tyr Ala Gly Val Gln His His Gly Leu Ser Tyr
        515                 520                 525 aac tgc tcc ctt ccg ctg gcg ttt gac ggg tct tgc tct ggc atc cag     1632
Asn Cys Ser Leu Pro Leu Ala Phe Asp Gly Ser Cys Ser Gly Ile Gln
    530                 535                 540 cac ttc tcc gcg atg ctc cga gat gag gta ggt ggt cgc gcg gtt aac     1680
His Phe Ser Ala Met Leu Arg Asp Glu Val Gly Gly Arg Ala Val Asn
545                 550                 555                 560 ttg ctt cct agt gaa acc gtt cag gac atc tac ggg att gtt gct aag     1728
Leu Leu Pro Ser Glu Thr Val Gln Asp Ile Tyr Gly Ile Val Ala Lys
                565                 570                 575 aaa gtc aac gag att cta caa gca gac gca atc aat ggg acc gat aac     1776
Lys Val Asn Glu Ile Leu Gln Ala Asp Ala Ile Asn Gly Thr Asp Asn
            580                 585                 590 gaa gta gtt acc gtg acc gat gag aac act ggt gaa atc tct gag aaa     1824
Glu Val Val Thr Val Thr Asp Glu Asn Thr Gly Glu Ile Ser Glu Lys
        595                 600                 605 gtc aag ctg ggc act aag gca ctg gct ggt caa tgg ctg gct tac ggt     1872
Val Lys Leu Gly Thr Lys Ala Leu Ala Gly Gln Trp Leu Ala Tyr Gly
    610                 615                 620 gtt act cgc agt gtg act aag cgt tca gtc atg acg ctg gct tac ggg     1920
Val Thr Arg Ser Val Thr Lys Arg Ser Val Met Thr Leu Ala Tyr Gly
625                 630                 635                 640 tcc aaa gag ttc ggc ttc cgt caa caa gtg ctg gaa gat acc att cag     1968
Ser Lys Glu Phe Gly Phe Arg Gln Gln Val Leu Glu Asp Thr Ile Gln
                645                 650                 655 cca gct att gat tcc ggc aag ggt ctg atg ttc act cag ccg aat cag     2016
Pro Ala Ile Asp Ser Gly Lys Gly Leu Met Phe Thr Gln Pro Asn Gln
            660                 665                 670 gct gct gga tac atg gct aag ctg att tgg gaa tct gtg agc gtg acg     2064
Ala Ala Gly Tyr Met Ala Lys Leu Ile Trp Glu Ser Val Ser Val Thr
        675                 680                 685 gtg gta gct gcg gtt gaa gca atg aac tgg ctt aag tct gct gct aag     2112
Val Val Ala Ala Val Glu Ala Met Asn Trp Leu Lys Ser Ala Ala Lys
    690                 695                 700 ctg ctg gct gct gag gtc aaa gat aag aag act gga gag att ctt cgc     2160
Leu Leu Ala Ala Glu Val Lys Asp Lys Lys Thr Gly Glu Ile Leu Arg
```

|  |  |  |  |  |  |  |  |  |  |  |  |  |
|---|---|---|---|---|---|---|---|---|---|---|---|---|
|  | 705 |  |  | 710 |  |  | 715 |  |  | 720 |  |  |
| aag | cgt | tgc | gct | gtg | cat | tgg | gta | act | cct | gat | ggt | ttc | cct | gtg | tgg | 2208 |
| Lys | Arg | Cys | Ala | Val | His | Trp | Val | Thr | Pro | Asp | Gly | Phe | Pro | Val | Trp |  |
|  |  |  |  | 725 |  |  |  |  | 730 |  |  |  |  | 735 |  |  |
| cag | gaa | tac | aag | aag | cct | att | cag | acg | cgc | ttg | aac | ctg | atg | ttc | ctc | 2256 |
| Gln | Glu | Tyr | Lys | Lys | Pro | Ile | Gln | Thr | Arg | Leu | Asn | Leu | Met | Phe | Leu |  |
|  |  |  | 740 |  |  |  |  | 745 |  |  |  |  | 750 |  |  |  |
| ggt | cag | ttc | cgc | tta | cag | cct | acc | att | aac | acc | aac | aaa | gat | agc | gag | 2304 |
| Gly | Gln | Phe | Arg | Leu | Gln | Pro | Thr | Ile | Asn | Thr | Asn | Lys | Asp | Ser | Glu |  |
|  |  | 755 |  |  |  |  | 760 |  |  |  |  | 765 |  |  |  |  |
| att | gat | gca | cac | aaa | cag | gag | tct | ggt | atc | gct | cct | aac | ttt | gta | cac | 2352 |
| Ile | Asp | Ala | His | Lys | Gln | Glu | Ser | Gly | Ile | Ala | Pro | Asn | Phe | Val | His |  |
|  | 770 |  |  |  |  | 775 |  |  |  |  | 780 |  |  |  |  |  |
| agc | caa | gac | ggt | agc | cac | ctt | cgt | aag | act | gta | gtg | tgg | gca | cac | gag | 2400 |
| Ser | Gln | Asp | Gly | Ser | His | Leu | Arg | Lys | Thr | Val | Val | Trp | Ala | His | Glu |  |
| 785 |  |  |  |  | 790 |  |  |  |  | 795 |  |  |  |  | 800 |  |
| aag | tac | gga | atc | gaa | tct | ttt | gca | ctg | aat | cac | gac | tcc | ttc | ggt | acc | 2448 |
| Lys | Tyr | Gly | Ile | Glu | Ser | Phe | Ala | Leu | Asn | His | Asp | Ser | Phe | Gly | Thr |  |
|  |  |  |  | 805 |  |  |  |  | 810 |  |  |  |  | 815 |  |  |
| att | ccg | gct | gac | gct | gcg | aac | ctg | ttc | aaa | gca | gtg | cgc | gaa | act | atg | 2496 |
| Ile | Pro | Ala | Asp | Ala | Ala | Asn | Leu | Phe | Lys | Ala | Val | Arg | Glu | Thr | Met |  |
|  |  |  | 820 |  |  |  |  | 825 |  |  |  |  | 830 |  |  |  |
| gtt | gac | aca | tat | gag | tct | tgt | gat | gta | ctg | gct | gat | ttc | tac | gac | cag | 2544 |
| Val | Asp | Thr | Tyr | Glu | Ser | Cys | Asp | Val | Leu | Ala | Asp | Phe | Tyr | Asp | Gln |  |
|  |  | 835 |  |  |  |  | 840 |  |  |  |  | 845 |  |  |  |  |
| ttc | gct | gac | cag | ttg | cac | gag | tct | caa | ttg | gac | aaa | atg | cca | gca | ctt | 2592 |
| Phe | Ala | Asp | Gln | Leu | His | Glu | Ser | Gln | Leu | Asp | Lys | Met | Pro | Ala | Leu |  |
|  | 850 |  |  |  |  | 855 |  |  |  |  | 860 |  |  |  |  |  |
| ccg | gct | aaa | ggt | aac | ttg | aac | ctc | cgt | gac | atc | tta | gag | tcg | gac | ttc | 2640 |
| Pro | Ala | Lys | Gly | Asn | Leu | Asn | Leu | Arg | Asp | Ile | Leu | Glu | Ser | Asp | Phe |  |
| 865 |  |  |  |  | 870 |  |  |  |  | 875 |  |  |  |  | 880 |  |
| gcg | ttc | gcg | taa |  |  |  |  |  |  |  |  |  |  |  |  | 2652 |
| Ala | Phe | Ala |  |  |  |  |  |  |  |  |  |  |  |  |  |  |

<210> SEQ ID NO 14
<211> LENGTH: 883
<212> TYPE: PRT
<213> ORGANISM: Artificial sequence
<220> FEATURE:
<223> OTHER INFORMATION: Description of the artificial sequence: mutated
      sequences of bacteriophage T7 RNA polymerase

<400> SEQUENCE: 14

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

-continued

```
Ala Asp Asn Thr Thr Val Gln Ala Val Ala Ser Ala Ile Gly Arg Ala
    130                 135                 140
Ile Glu Asp Glu Ala Arg Phe Gly Arg Ile Arg Asp Leu Glu Ala Lys
145                 150                 155                 160
His Phe Lys Lys Asn Val Glu Gln Leu Asn Lys Arg Val Gly His
                165                 170                 175
Val Tyr Lys Lys Ala Phe Met Gln Val Glu Ala Asp Met Leu Ser
            180                 185                 190
Lys Gly Leu Leu Gly Gly Glu Ala Trp Ser Ser Trp His Lys Glu Asp
        195                 200                 205
Ser Ile His Val Gly Val Arg Cys Ile Glu Met Leu Ile Glu Ser Thr
    210                 215                 220
Gly Met Val Ser Leu His Arg Gln Asn Ala Gly Val Val Gly Gln Asp
225                 230                 235                 240
Ser Glu Thr Ile Glu Leu Ala Pro Glu Tyr Ala Glu Ala Ile Ala Thr
                245                 250                 255
Arg Ala Gly Ala Leu Ala Gly Ile Ser Leu Met Phe Gln Pro Cys Val
            260                 265                 270
Val Pro Pro Lys Pro Trp Thr Gly Ile Thr Gly Gly Tyr Trp Ala
        275                 280                 285
Asn Gly Arg Arg Pro Leu Ala Leu Val Arg Thr His Ser Lys Lys Ala
    290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
                325                 330                 335
Val Ala Asn Val Ile Thr Lys Trp Lys His Cys Pro Val Glu Asp Ile
            340                 345                 350
Pro Ala Ile Glu Arg Glu Leu Pro Met Lys Pro Glu Asp Ile Asp
        355                 360                 365
Met Asn Pro Glu Ala Leu Thr Ala Trp Lys Arg Ala Ala Ala Val
    370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
            420                 425                 430
Asn Pro Gln Gly Asn Asp Met Thr Lys Gly Leu Leu Thr Leu Ala Lys
        435                 440                 445
Gly Lys Pro Ile Gly Lys Glu Gly Tyr Tyr Trp Leu Lys Ile His Gly
    450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
        515                 520                 525
Asn Cys Ser Leu Pro Leu Ala Phe Asp Gly Ser Cys Ser Gly Ile Gln
    530                 535                 540
```

```
His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
        580                 585                 590

Glu Val Val Thr Val Thr Asp Glu Asn Thr Gly Glu Ile Ser Glu Lys
    595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
        660                 665                 670

Ala Ala Gly Tyr Met Ala Lys Leu Ile Trp Glu Ser Val Ser Val Thr
    675                 680                 685

Val Val Ala Ala Val Glu Ala Met Asn Trp Leu Lys Ser Ala Ala Lys
690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
        740                 745                 750

Gly Gln Phe Arg Leu Gln Pro Thr Ile Asn Thr Asn Lys Asp Ser Glu
    755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Asn His Asp Ser Phe Gly Thr
            805                 810                 815

Ile Pro Ala Asp Ala Ala Asn Leu Phe Lys Ala Val Arg Glu Thr Met
        820                 825                 830

Val Asp Thr Tyr Glu Ser Cys Asp Val Leu Ala Asp Phe Tyr Asp Gln
    835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 15
<211> LENGTH: 2652
<212> TYPE: DNA
<213> ORGANISM: Artificial sequence
<220> FEATURE:
<223> OTHER INFORMATION: Description of the artificial sequence: mutated
      sequences of bacteriophage T7 RNA polymerase
<220> FEATURE:
<221> NAME/KEY: CDS
<222> LOCATION: (1)..(2652)

<400> SEQUENCE: 15
```

-continued

| | |
|---|---|
| atg aac acg att aac atc gct aag aac gac ttc tct gac atc gaa ctg<br>Met Asn Thr Ile Asn Ile Ala Lys Asn Asp Phe Ser Asp Ile Glu Leu<br>1               5                   10                  15 | 48 |
| gct gct atc ccg ttc aac act ctg gct gac cat tac ggt gag cgt tta<br>Ala Ala Ile Pro Phe Asn Thr Leu Ala Asp His Tyr Gly Glu Arg Leu<br>            20                  25                  30 | 96 |
| gct cgc gaa cag ttg gcc ctt gag cat gag tct tac gag atg ggt gaa<br>Ala Arg Glu Gln Leu Ala Leu Glu His Glu Ser Tyr Glu Met Gly Glu<br>        35                  40                  45 | 144 |
| gca cgc ttc cgc aag atg ttt gag cgt caa ctt aaa gct ggt gag gtt<br>Ala Arg Phe Arg Lys Met Phe Glu Arg Gln Leu Lys Ala Gly Glu Val<br>    50                  55                  60 | 192 |
| gcg gat aac gct gcc gcc aag cct ctc atc act acc cta ctc cct aag<br>Ala Asp Asn Ala Ala Ala Lys Pro Leu Ile Thr Thr Leu Leu Pro Lys<br>65                  70                  75                  80 | 240 |
| atg att gca cgc atc aac gac tgg ttt gag gaa gtg aaa gct aag cgc<br>Met Ile Ala Arg Ile Asn Asp Trp Phe Glu Glu Val Lys Ala Lys Arg<br>                85                  90                  95 | 288 |
| ggc aag cgc ccg aca gcc ttc cag ttc ctg caa gaa atc aag ccg gaa<br>Gly Lys Arg Pro Thr Ala Phe Gln Phe Leu Gln Glu Ile Lys Pro Glu<br>            100                 105                 110 | 336 |
| gcc gta gcg tac atc acc gtt aag acc act ctg gct tgc cta acc agt<br>Ala Val Ala Tyr Ile Thr Val Lys Thr Thr Leu Ala Cys Leu Thr Ser<br>        115                 120                 125 | 384 |
| gct gac aat aca acc gtt cag gct gta gca agc gca atc ggt cgg gcc<br>Ala Asp Asn Thr Thr Val Gln Ala Val Ala Ser Ala Ile Gly Arg Ala<br>    130                 135                 140 | 432 |
| att gag aac gag gct cgc ttc ggt cgt atc cgt gac ctt gaa gct aag<br>Ile Glu Asn Glu Ala Arg Phe Gly Arg Ile Arg Asp Leu Glu Ala Lys<br>145                 150                 155                 160 | 480 |
| cac ttc aag aaa aac gtt gag gaa caa ctc aac aag cgc gta ggg cac<br>His Phe Lys Lys Asn Val Glu Glu Gln Leu Asn Lys Arg Val Gly His<br>                165                 170                 175 | 528 |
| gtc tac aag aaa gca ttt atg caa gtt gtc gag gct gac atg ctc tct<br>Val Tyr Lys Lys Ala Phe Met Gln Val Val Glu Ala Asp Met Leu Ser<br>            180                 185                 190 | 576 |
| aag ggt cta ctc ggt ggc gag gcg tgg tct tcg tgg cat aag gaa gac<br>Lys Gly Leu Leu Gly Gly Glu Ala Trp Ser Ser Trp His Lys Glu Asp<br>        195                 200                 205 | 624 |
| tct att cat gta gga gta cgc tgc atc gag atg ctc att gag tca acc<br>Ser Ile His Val Gly Val Arg Cys Ile Glu Met Leu Ile Glu Ser Thr<br>    210                 215                 220 | 672 |
| gga atg gtt agc tta cac cgc caa aat gct ggc gta gta ggt caa gac<br>Gly Met Val Ser Leu His Arg Gln Asn Ala Gly Val Val Gly Gln Asp<br>225                 230                 235                 240 | 720 |
| tct gag act atc gaa ctc gca cct gaa tac gct gag gct atc gca acc<br>Ser Glu Thr Ile Glu Leu Ala Pro Glu Tyr Ala Glu Ala Ile Ala Thr<br>                245                 250                 255 | 768 |
| cgt gca ggt gcg ctg gct ggc atc tct ccg atg ttc caa cct tgc gta<br>Arg Ala Gly Ala Leu Ala Gly Ile Ser Pro Met Phe Gln Pro Cys Val<br>            260                 265                 270 | 816 |
| gtt cct cct aag ccg tgg act ggc att act ggt ggt ggc tat tgg gct<br>Val Pro Pro Lys Pro Trp Thr Gly Ile Thr Gly Gly Gly Tyr Trp Ala<br>        275                 280                 285 | 864 |
| aac ggt cgt cgt cct ctg gcg ctg gtg cgt act cac agt aag aaa gca<br>Asn Gly Arg Arg Pro Leu Ala Leu Val Arg Thr His Ser Lys Lys Ala<br>    290                 295                 300 | 912 |
| ctg atg cgc tac gaa gac gtt tac atg cct gag gtg tac aaa gcg att<br>Leu Met Arg Tyr Glu Asp Val Tyr Met Pro Glu Val Tyr Lys Ala Ile<br>305                 310                 315                 320 | 960 |

```
aac att gcg caa aac acc gca tgg aaa atc aac aag aaa gtc cta gcg    1008
Asn Ile Ala Gln Asn Thr Ala Trp Lys Ile Asn Lys Lys Val Leu Ala
            325                 330                 335 gtc gcc aac gta atc acc aag tgg aag cat tgt ccg gtc gag gac atc    1056
Val Ala Asn Val Ile Thr Lys Trp Lys His Cys Pro Val Glu Asp Ile
            340                 345                 350 cct gcg att gag cgt gaa gaa ctc ccg atg aaa ccg gaa gac atc gac    1104
Pro Ala Ile Glu Arg Glu Glu Leu Pro Met Lys Pro Glu Asp Ile Asp
            355                 360                 365 atg aat cct gag gct ctc acc gcg tgg aaa cgt gct gcc gct gct gtg    1152
Met Asn Pro Glu Ala Leu Thr Ala Trp Lys Arg Ala Ala Ala Ala Val
        370                 375                 380 tac cgc aag gac aag gct cgc aag tct cgc cgt atc agc ctt gag ttc    1200
Tyr Arg Lys Asp Lys Ala Arg Lys Ser Arg Arg Ile Ser Leu Glu Phe
385                 390                 395                 400 atg ctt gag caa gcc aat aag ttt gct aac cat aag gcc atc tgg ttc    1248
Met Leu Glu Gln Ala Asn Lys Phe Ala Asn His Lys Ala Ile Trp Phe
            405                 410                 415 cct tac aac atg gac tgg cgc ggt cgt gtt tac gct gtg tca atg ttc    1296
Pro Tyr Asn Met Asp Trp Arg Gly Arg Val Tyr Ala Val Ser Met Phe
        420                 425                 430 aac ccg caa ggt aac gat atg acc aaa gga ctg ctt acg ctg gcg aaa    1344
Asn Pro Gln Gly Asn Asp Met Thr Lys Gly Leu Leu Thr Leu Ala Lys
        435                 440                 445 ggt aaa cca atc ggt aag gaa ggt tac tac tgg ctg aaa atc cac ggt    1392
Gly Lys Pro Ile Gly Lys Glu Gly Tyr Tyr Trp Leu Lys Ile His Gly
    450                 455                 460 gca aac tgt gcg ggt gtc gat aag gtt ccg ttc cct gag cgc atc aag    1440
Ala Asn Cys Ala Gly Val Asp Lys Val Pro Phe Pro Glu Arg Ile Lys
465                 470                 475                 480 ttc att gag gaa aac cac gag aac atc atg gct tgc gct aag tct cca    1488
Phe Ile Glu Glu Asn His Glu Asn Ile Met Ala Cys Ala Lys Ser Pro
            485                 490                 495 ctg gag aac act tgg tgg gct gag caa gat tct ccg ttc tgc ttc ctt    1536
Leu Glu Asn Thr Trp Trp Ala Glu Gln Asp Ser Pro Phe Cys Phe Leu
        500                 505                 510 gcg ttc tgc ttt gag tac gct ggg gta cag cac cac ggc ctg agc tat    1584
Ala Phe Cys Phe Glu Tyr Ala Gly Val Gln His His Gly Leu Ser Tyr
        515                 520                 525 aac tgc tcc ctt ccg ctg gcg ttt gac ggg tct tgc tct ggc atc cag    1632
Asn Cys Ser Leu Pro Leu Ala Phe Asp Gly Ser Cys Ser Gly Ile Gln
    530                 535                 540 cac ttc tcc gcg atg ctc cga gat gag gta ggt ggt cgc gcg gtt aac    1680
His Phe Ser Ala Met Leu Arg Asp Glu Val Gly Gly Arg Ala Val Asn
545                 550                 555                 560 ttg ctt cct agt gaa acc gtt cag gac atc tac ggg att gtt gct aag    1728
Leu Leu Pro Ser Glu Thr Val Gln Asp Ile Tyr Gly Ile Val Ala Lys
            565                 570                 575 aaa gtc aac gag att cta caa gca gac gca atc aat ggg acc gat aac    1776
Lys Val Asn Glu Ile Leu Gln Ala Asp Ala Ile Asn Gly Thr Asp Asn
            580                 585                 590 gaa gta gtt acc gtg acc gat gag aac act ggt gaa atc tct gag aaa    1824
Glu Val Val Thr Val Thr Asp Glu Asn Thr Gly Glu Ile Ser Glu Lys
        595                 600                 605 gtc aag ctg ggc act aag gca ctg gct ggt caa tgg ctg gct tac ggt    1872
Val Lys Leu Gly Thr Lys Ala Leu Ala Gly Gln Trp Leu Ala Tyr Gly
        610                 615                 620 gtt act cgc agt gtg act aag cgt tca gtc atg acg ctg gct tac ggg    1920
Val Thr Arg Ser Val Thr Lys Arg Ser Val Met Thr Leu Ala Tyr Gly
```

```
                    625             630             635             640
tcc aaa gag ttc ggc ttc cgt caa caa gtg ctg gaa gat acc att cag       1968
Ser Lys Glu Phe Gly Phe Arg Gln Gln Val Leu Glu Asp Thr Ile Gln
                    645             650             655 cca gct att gat tcc ggc aag ggt ctg atg ttc act cag ccg aat cag       2016
Pro Ala Ile Asp Ser Gly Lys Gly Leu Met Phe Thr Gln Pro Asn Gln
                660             665             670 gct gct gga tac atg gct aag ctg att tgg gaa tct gtg agc gtg acg       2064
Ala Ala Gly Tyr Met Ala Lys Leu Ile Trp Glu Ser Val Ser Val Thr
            675             680             685 gtg gta gct gcg gtt gaa gca atg aac tgg ctt aag tct gct gct aag       2112
Val Val Ala Ala Val Glu Ala Met Asn Trp Leu Lys Ser Ala Ala Lys
        690             695             700 ctg ctg gct gct gag gtc aaa gat aag aag act gga gag att ctt cgc       2160
Leu Leu Ala Ala Glu Val Lys Asp Lys Lys Thr Gly Glu Ile Leu Arg
705             710             715             720 aag cgt tgc gct gtg cat tgg gta act cct gat ggt ttc cct gtg tgg       2208
Lys Arg Cys Ala Val His Trp Val Thr Pro Asp Gly Phe Pro Val Trp
            725             730             735 cag gaa tac aag aag cct att cag acg cgc ttg aac ctg atg ttc ctc       2256
Gln Glu Tyr Lys Lys Pro Ile Gln Thr Arg Leu Asn Leu Met Phe Leu
        740             745             750 ggt cag ttc cgc tta cag cct acc att aac acc aac aaa gat agc gag       2304
Gly Gln Phe Arg Leu Gln Pro Thr Ile Asn Thr Asn Lys Asp Ser Glu
    755             760             765 att gat gca cac aaa cag gag tct ggt atc gct cct aac ttt gta cac       2352
Ile Asp Ala His Lys Gln Glu Ser Gly Ile Ala Pro Asn Phe Val His
770             775             780 agc caa gac ggt agc cac ctt cgt aag act gta gtg tgg gca cac gag       2400
Ser Gln Asp Gly Ser His Leu Arg Lys Thr Val Val Trp Ala His Glu
785             790             795             800 aag tac gga atc gaa tct ttt gca ctg aat cac gac tcc ttc ggt acc       2448
Lys Tyr Gly Ile Glu Ser Phe Ala Leu Asn His Asp Ser Phe Gly Thr
            805             810             815 att ccg gct gac gct gcg aac ctg ttc aaa gca gtg cgc gaa act atg       2496
Ile Pro Ala Asp Ala Ala Asn Leu Phe Lys Ala Val Arg Glu Thr Met
        820             825             830 gtt gac aca tat gag tct tgt gat gta ctg gct gat ttc tac gac cag       2544
Val Asp Thr Tyr Glu Ser Cys Asp Val Leu Ala Asp Phe Tyr Asp Gln
    835             840             845 ttc gct gac cag ttg cac gag tct caa ttg gac aaa atg cca gca ctt       2592
Phe Ala Asp Gln Leu His Glu Ser Gln Leu Asp Lys Met Pro Ala Leu
850             855             860 ccg gct aaa ggt aac ttg aac ctc cgt gac atc tta gag tcg gac ttc       2640
Pro Ala Lys Gly Asn Leu Asn Leu Arg Asp Ile Leu Glu Ser Asp Phe
865             870             875             880 gcg ttc gcg taa                                                       2652
Ala Phe Ala
```

<210> SEQ ID NO 16
<211> LENGTH: 883
<212> TYPE: PRT
<213> ORGANISM: Artificial sequence
<220> FEATURE:
<223> OTHER INFORMATION: Description of the artificial sequence: mutated sequences of bacteriophage T7 RNA polymerase

<400> SEQUENCE: 16

```
Met Asn Thr Ile Asn Ile Ala Lys Asn Asp Phe Ser Asp Ile Glu Leu
1               5                   10                  15
```

```
Ala Ala Ile Pro Phe Asn Thr Leu Ala Asp His Tyr Gly Glu Arg Leu
         20                  25                  30

Ala Arg Glu Gln Leu Ala Leu Glu His Glu Ser Tyr Glu Met Gly Glu
         35                  40                  45

Ala Arg Phe Arg Lys Met Phe Glu Arg Gln Leu Lys Ala Gly Glu Val
         50                  55                  60

Ala Asp Asn Ala Ala Lys Pro Leu Ile Thr Thr Leu Leu Pro Lys
 65                  70                  75                  80

Met Ile Ala Arg Ile Asn Asp Trp Phe Glu Val Lys Ala Lys Arg
                 85                  90                  95

Gly Lys Arg Pro Thr Ala Phe Gln Phe Leu Gln Glu Ile Lys Pro Glu
             100                 105                 110

Ala Val Ala Tyr Ile Thr Val Lys Thr Leu Ala Cys Leu Thr Ser
             115                 120                 125

Ala Asp Asn Thr Thr Val Gln Ala Val Ala Ser Ala Ile Gly Arg Ala
 130                 135                 140

Ile Glu Asn Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                 165                 170                 175

Val Tyr Lys Lys Ala Phe Met Gln Val Val Glu Ala Asp Met Leu Ser
             180                 185                 190

Lys Gly Leu Leu Gly Gly Glu Ala Trp Ser Ser Trp His Lys Glu Asp
             195                 200                 205

Ser Ile His Val Gly Val Arg Cys Ile Glu Met Leu Ile Glu Ser Thr
 210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                 245                 250                 255

Arg Ala Gly Ala Leu Ala Gly Ile Ser Pro Met Phe Gln Pro Cys Val
             260                 265                 270

Val Pro Pro Lys Pro Trp Thr Gly Ile Thr Gly Gly Tyr Trp Ala
             275                 280                 285

Asn Gly Arg Arg Pro Leu Ala Leu Val Arg Thr His Ser Lys Lys Ala
 290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                 325                 330                 335

Val Ala Asn Val Ile Thr Lys Trp Lys His Cys Pro Val Glu Asp Ile
             340                 345                 350

Pro Ala Ile Glu Arg Glu Glu Leu Pro Met Lys Pro Glu Asp Ile Asp
             355                 360                 365

Met Asn Pro Glu Ala Leu Thr Ala Trp Lys Arg Ala Ala Ala Val
             370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                 405                 410                 415

Pro Tyr Asn Met Asp Trp Arg Gly Arg Val Tyr Ala Val Ser Met Phe
             420                 425                 430

Asn Pro Gln Gly Asn Asp Met Thr Lys Gly Leu Leu Thr Leu Ala Lys
```

```
                435             440             445
Gly Lys Pro Ile Gly Lys Glu Gly Tyr Tyr Trp Leu Lys Ile His Gly
450             455             460

Ala Asn Cys Ala Gly Val Asp Lys Val Pro Phe Pro Glu Arg Ile Lys
465             470             475             480

Phe Ile Glu Glu Asn His Glu Asn Ile Met Ala Cys Ala Lys Ser Pro
                485             490             495

Leu Glu Asn Thr Trp Trp Ala Glu Gln Asp Ser Pro Phe Cys Phe Leu
            500             505             510

Ala Phe Cys Phe Glu Tyr Ala Gly Val Gln His His Gly Leu Ser Tyr
            515             520             525

Asn Cys Ser Leu Pro Leu Ala Phe Asp Gly Ser Cys Ser Gly Ile Gln
530             535             540

His Phe Ser Ala Met Leu Arg Asp Glu Val Gly Gly Arg Ala Val Asn
545             550             555             560

Leu Leu Pro Ser Glu Thr Val Gln Asp Ile Tyr Gly Ile Val Ala Lys
                565             570             575

Lys Val Asn Glu Ile Leu Gln Ala Asp Ala Ile Asn Gly Thr Asp Asn
            580             585             590

Glu Val Val Thr Val Thr Asp Glu Asn Thr Gly Glu Ile Ser Glu Lys
            595             600             605

Val Lys Leu Gly Thr Lys Ala Leu Ala Gly Gln Trp Leu Ala Tyr Gly
610             615             620

Val Thr Arg Ser Val Thr Lys Arg Ser Val Met Thr Leu Ala Tyr Gly
625             630             635             640

Ser Lys Glu Phe Gly Phe Arg Gln Gln Val Leu Glu Asp Thr Ile Gln
                645             650             655

Pro Ala Ile Asp Ser Gly Lys Gly Leu Met Phe Thr Gln Pro Asn Gln
            660             665             670

Ala Ala Gly Tyr Met Ala Lys Leu Ile Trp Glu Ser Val Ser Val Thr
            675             680             685

Val Val Ala Ala Val Glu Ala Met Asn Trp Leu Lys Ser Ala Ala Lys
690             695             700

Leu Leu Ala Ala Glu Val Lys Asp Lys Lys Thr Gly Glu Ile Leu Arg
705             710             715             720

Lys Arg Cys Ala Val His Trp Val Thr Pro Asp Gly Phe Pro Val Trp
                725             730             735

Gln Glu Tyr Lys Lys Pro Ile Gln Thr Arg Leu Asn Leu Met Phe Leu
            740             745             750

Gly Gln Phe Arg Leu Gln Pro Thr Ile Asn Thr Asn Lys Asp Ser Glu
            755             760             765

Ile Asp Ala His Lys Gln Glu Ser Gly Ile Ala Pro Asn Phe Val His
770             775             780

Ser Gln Asp Gly Ser His Leu Arg Lys Thr Val Val Trp Ala His Glu
785             790             795             800

Lys Tyr Gly Ile Glu Ser Phe Ala Leu Asn His Asp Ser Phe Gly Thr
                805             810             815

Ile Pro Ala Asp Ala Ala Asn Leu Phe Lys Ala Val Arg Glu Thr Met
            820             825             830

Val Asp Thr Tyr Glu Ser Cys Asp Val Leu Ala Asp Phe Tyr Asp Gln
            835             840             845

Phe Ala Asp Gln Leu His Glu Ser Gln Leu Asp Lys Met Pro Ala Leu
850             855             860
```

```
Pro Ala Lys Gly Asn Leu Asn Leu Arg Asp Ile Leu Glu Ser Asp Phe
865                 870                 875                 880

Ala Phe Ala
```